United States Patent [19]

Amuti

[11] Patent Number: 5,332,718

[45] Date of Patent: Jul. 26, 1994

[54] HERBICIDAL SUBSTITUTED BICYCLIC TRIAZOLES FOR PLANTATION CROPS

[75] Inventor: Kofi S. Amuti, Wilmington, Del.

[73] Assignee: E. I. Du Pont de Nemours and Company, Wilmington, Del.

[21] Appl. No.: 30,099

[22] Filed: Mar. 15, 1993

[51] Int. Cl.⁵ .................. A01N 43/42; A01N 43/653
[52] U.S. Cl. .................................... 504/246; 504/139
[58] Field of Search ............... 504/246; A01N 43/653

[56] References Cited

U.S. PATENT DOCUMENTS

| | | | |
|---|---|---|---|
| 4,213,773 | 7/1980 | Wolf | 71/92 |
| 4,881,967 | 11/1989 | Semple | 71/92 |
| 4,925,481 | 5/1990 | Blume et al. | 71/92 |

FOREIGN PATENT DOCUMENTS 430385 11/1990 European Pat. Off. .

Primary Examiner—Richard L. Raymond
Assistant Examiner—S. Mark Clardy

[57] ABSTRACT

This invention relates to substituted bicyclic triazoles of Formula I which are useful as herbicides.

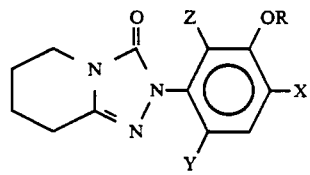

12 Claims, No Drawings

HERBICIDAL SUBSTITUTED BICYCLIC TRIAZOLES FOR PLANTATION CROPS

CROSS-REFERENCE TO RELATED APPLICATION

This application is a continuation under 35 USC 371 of international application PCT/US91/06372, with an international filing date of Sep. 11, 1991, and international priority based on U.S. Ser. No. 07/581,994, filed Sep. 13, 1990 now abandoned.

BACKGROUND OF THE INVENTION

The compounds of the instant invention are known for use as herbicides. Such disclosure is found in U.S. Pat. No. 4,213,773 and U.S. Pat. No. 4,881,967. These patents, however, do not teach use of such herbicides on plantation crops. Plantation crops are an important market and crops such as citrus, sugarcane, coffee, banana, oil palm, etc. are very important to mankind's diet. Also, plantation crops such as rubber are an important source of an industrial raw material. These crops are cultivated particularly in regions of the Pacific rim and South America. A need therefore exists for herbicidal material which are useful for treating plantation crops such as those mentioned.

SUMMARY OF THE INVENTION

This invention comprises the novel use of the compound of Formula I and their agriculturally suitable salts for broad spectrum weed control in plantation crops.

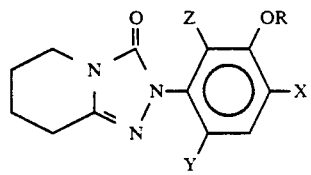
I wherein
R is isopropyl, allyl, propargyl or —CH(CH₃)C≡CH;
X is Cl or Br;
Y is F or Cl;
Z is H or can be taken together with R as

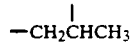

such that the linking oxygen is attached to the methane carbon;

Preferred for reasons of more efficient weed control and/or better crop tolerance are:

1. A method for controlling undesired weeds in plantation crops which comprises applying to the locus of the weeds a herbicidally effective amount of a compound of Formula I wherein X is Cl, Y is Cl and Z is H.
2. A method of Preferred 1 wherein the plantation crop is selected from citrus, sugarcane, coffee, banana and loblolly pine.
3. A method of Preferred 1 wherein the compound is 2-[2,4-dichloro-5-[(2-propynyl)oxy]phenyl]-5,6,7,8-tetrahydro-1,2,4-triazolo-[4,3-a]-pyridin-3(H)-one.
4. A method of Preferred 3 wherein the plantation crop is citrus.
5. A method of Preferred 3 wherein the plantation crop is sugarcane.
6. A method of Preferred 3 wherein the plantation crop is coffee.
7. A method of Preferred 3 wherein the plantation crop is banana.
8. A method of Preferred 3 wherein the plantation crop is loblolly pine and the compound is applied preemergent.

DETAILED DESCRIPTION OF THE INVENTION

Synthesis

The compounds of Formula I can be prepared according to the procedures of U.S. Pat. No. 4,213,773 and U.S. Pat. No. 4,881,967. The disclosure of which are herein incorporated by reference.

Particularly important compounds for use in this invention include the following:

TABLE 1

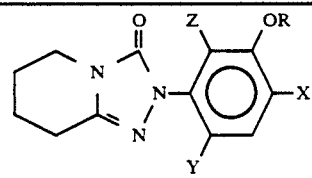

| X | Y | Z | R |
|---|---|---|---|
| Cl | Cl | H | —CH₂C≡CH |
| Cl | Cl | H | —CH₂CH=CH₂ |
| Cl | Cl | H | —CH(CH₃)C≡CH |
| Cl | Cl | H | —CH(CH₃)₂ |
| Cl | Cl |   | —CH₂CHCH₃ (bridged) |
| Cl | F | H | —CH₂C≡CH |
| Cl | F | H | —CH₂CH=CH₂ |
| Cl | F | H | —CH(CH₃)C≡CH |
| Cl | F | H | —CH(CH₃)₂ |
| Cl | F |   | —CH₂CHCH₃ (bridged) |
| Br | Cl | H | —CH₂C≡CH |
| Br | Cl | H | —CH₂CH=CH₂ |
| Br | Cl | H | —CH(CH₃)C≡CH |
| Br | Cl | H | —CH(CH₃)₂ |
| Br | Cl |   | —CH₂CHCH₃ (bridged) |
| Br | F | H | —CH₂C≡CH |
| Br | F | H | —CH₂CH=CH₂ |
| Br | F | H | —CH(CH₃)C≡CH |
| Br | F | H | —CH(CH₃)₂ |
| Br | F |   | —CH₂CHCH₃ (bridged) |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

|  | Weight Percent* | | |
| --- | --- | --- | --- |
|  | Active Ingredient | Diluent(s) | Surfactant(s) |
| Wettable Powders | 20-90 | 0-74 | 1-10 |
| Oil Suspensions, Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength Compositions | 90-99 | 0-10 | 0-2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide", 2nd Ed., Interscience, N.Y., 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., N.Y., 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, ginding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, N.Y., 1973, pp. 8-57ff.

For further information regarding the art of formulation, see for example:
H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138-140, 162-164, 166, 167 and 169-182;

H. Gysin and E. Knusli, U.S. Pat. No. 2,891,855, Jun. 23, 1959, Col. 3, line 66 through Col. 5, line 17 and Examples 1-4;

G. C. Klingman, "Weed Control as a Science", John Wiley and Sons, Inc., New York, 1961, pp. 81-96; and J. D. Fryer and S. A. Evans, "Weed Control Handbook", 5th Ed., Blackwell Scientific Publications, Oxford, 1968, pp. 101-103.

In the following examples, all parts are by weight unless otherwise indicated.

EXAMPLE A

| Wettable Powder | |
| --- | --- |
| 2-[2,4-dichloro-5-[(2-propynyl)oxy]phenyl]-5,6,7,8-tetrahydro-1,2,4-triazolo-[4,3-a]-pyridin-3(H)-one | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE B

| Wettable Powder | |
| --- | --- |
| 2-[2,4-dichloro-5-[(2-propynyl)oxy]phenyl]-5,6,7,8-tetrahydro-1,2,4-triazolo-[4,3-a]-pyridin-3(H)-one | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE C

| Granule | |
| --- | --- |
| Wettable Powder of Example 11 | 5% |
| attapulgite granules (U.S.S. 20-40 mesh; 0.84-0.42 mm) | 95% |

A slurry of wettable powder containing 25% solids is sprayed on the surface of attapulgite granules in a double-cone blender. The granules are dried and packaged.

EXAMPLE D

| Extruded Pellet | |
| --- | --- |
| 2-[2,4-dichloro-5-[(2-propynyl)oxy]phenyl]-5,6,7,8-tetrahydro-1,2;4-triazolo-[4,3-a]-pyridin-3(H)-one | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE E

| Low Strength Granule | |
|---|---|
| 2-[2,4-dichloro-5-[(2-propynyl)oxy]phenyl]-5,6,7,8-tetrahydro-1,2,4-triazolo-[4,3-a]-pyridin-3(H)-one | 1% |
| N,N-dimethylformamide | 9% |
| attapulgite granules (U.S.S. 20 to 40 sieve) | 90% |

The active ingredient is dissolved in the solvent and the solution is sprayed upon dedusted granules in a double-cone blender. After spraying of the solution has been completed, the blender is allowed to run for a short period and then the granules are packaged.

EXAMPLE F

| Granule | |
|---|---|
| 2-[2,4-dichloro-5-[(2-propynyl)oxy]phenyl]-5,6,7,8-tetrahydro-1,2,4-triazolo-[4,3-a]-pyridin-3(H)-one | 80% |
| wetting agent | 1% |
| crude ligninsulfonate salt (containing 5-20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE G

| Aqueous Suspension | |
|---|---|
| 2-[2,4-dichloro-5-[(2-propynyl)oxy]phenyl]-5,6,7,8-tetrahydro-1,2,4-triazolo-[4,3-a]-pyridin-3(H)-one | 40% |
| polyacrylic acid thickener | 0.3% |
| dodecylphenol polyethylene glycol ether | 0.5% |
| disodium phosphate | .1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE H

| High Strength Concentrate | |
|---|---|
| 2-[2,4-dichloro-5-[(2-propynyl)oxy]phenyl]-5,6,7,8-tetrahydro-1,2,4-triazolo-[4,3-a]-pyridin-3(H)-one | 99% |
| silica aerogel | 0.5% |

| -continued | |
|---|---|
| High Strength Concentrate | |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE I

| Wettable Powder | |
|---|---|
| 2-[2,4-dichloro-5-[(2-propynyl)oxy]phenyl]-5,6,7,8-tetrahydro-1,2,4-triazolo-[4,3-a]-pyridin-3(H)-one | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE J

| Wettable Powder | |
|---|---|
| 2-[2,4-dichloro-5-[(2-propynyl)oxy]phenyl]-5,6,7,8-tetrahydro-1,2,4-triazolo-[4,3-a]-pyridin-3(H)-one | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE K

| Oil Suspension | |
|---|---|
| 2-[2,4-dichloro-5-[(2-propynyl)oxy]phenyl]-5,6,7,8-tetrahydro-1,2,4-triazolo-[4,3-a]-pyridin-3(H)-one | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE L

| Dust | |
|---|---|
| 2-[2,4-dichloro-5-[(2-propynyl)oxy]phenyl]-5,6,7,8-tetrahydro-1,2,4-triazolo-[4,3-a]-pyridin-3(H)-one | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

EXAMPLE M

| Oil Suspension | |
|---|---|
| 2-[2,4-dichloro-5-[(2-propynyl)oxy]phenyl]-5,6,7,8-tetrahydro-1,2,4-triazolo-[4,3-a]-pyridin-3(H)-one | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

UTILITY

The compounds of the present invention are active herbicides for selective and/or general broadleaf and grass weeds control in all plantation crops including coffee, cocoa, oil palm, rubber, sugarcane, citrus, grapes, fruit trees, nut trees, banana, plantain, pineapple, conifers, e.g., loblolly pine, and turf species Kentucky bluegrass, St. Augustine grass, Kentucky fescue and bermudagrass.

The compounds can be applied as a preemergence or postemergence treatment using techniques of banding, directed sprays or broadcast applications. By selecting the appropriate rate which would be apparent to one skilled in the art, the compounds of this invention can be used in areas where complete control of oil vegetation is desired, such as around fuel storage tanks, ammunition depots, industrial storage areas, oil well sites, drive-in theaters, around billboards, highway and railroad structures and in fence rows. Alternatively, by selecting the proper rates and adjuvants, the compounds of this invention can be used for selective weeds control in plantation crops such as citrus, sugarcane, coffee, oil palm, rubber, cocoa, grapes, fruit trees, pineapple, and turf species such as St. Augustine grass, Kentucky bluegrass, bermudagrass, Kentucky fescue. In general, the compounds of this invention are used at 5 to 5000 g/ha with a preferred rate range of 10 to 2000 g/ha rate. One skilled in the art can select the proper rates for a given situation.

The compounds of this invention may be used in combination with other herbicides listed below. They are particularly useful in combinations for total vegetation control in plantation crops including: triazine, triazole, uracil, urea, amide, carbamate, bipyridylium, phenoxy, sulfonylurea and imidazole types. They may also be used in combination with mefluidide, glyphosate or gluphosinate.

| Common Name | Chemical Name |
|---|---|
| acetochlor | 2-chloro-N-(ethoxymethyl)-N-(2-ethyl-6-methylphenyl)acetamide |
| acifluorfen | 5-[2-chloro-4-(trifluoromethyl)phenoxy]-2-nitrobenzoic acid |
| acrolein | 2-propenal |
| alachlor | 2-chloro-N-(2,6-diethylphenyl)-N-methoxymethyl)acetamide |
| anilofos | S-4-chloro-N-isopropylcarbaniloymethyl-O,O-dimethyl phosphorodithioate |
| ametryn | N-ethyl-N'-(1-methylethyl)-6-(methylthio)-1,3,5-triazine-2,4-diamine |
| amitrole | 1H-1,2,4-triazol-3-amine |
| AMS | ammonium sulfamate |
| asulam | methyl[(4-aminophenyl)sulfonyl]carbamate |
| atrazine | 6-chloro-N-ethyl-N'-(1-methylethyl)-1,3,5-triazine-2,4-diamine |
| barban | 4-chloro-2-butynyl 3-chlorocarbamate |
| benefin | N-butyl-N-ethyl-2,6-dinitro-4-(trifluoromethyl)benzenamine |
| bensulfuron methyl | 2-[[[[[(4,6-dimethoxy-2-pyrimidinyl)amino]methylcarbonyl]amino]sulfonyl]methyl]benzoic acid, methyl ester |
| bensulide | O,O-bis(1-methylethyl)S-[2-[(phenylsulfonyl)amino]ethyl]phosphorodithioate |
| bentazon | 3-(1-methylethyl)-(1H)-2,1,3-benzothiadiazin-4(3H)-one, 2,2-dioxide |
| benzofluor | N-[4-(ethylthio)-2-(trifluoromethyl)phenyl]-methanesulfonamide |
| benzoylprop | N-benzoyl-N-(3,4-dichlorophenyl)-DL-alanine |
| bifenox | methyl 5-(2,4-dichlorophenoxy)-2-nitrobenzoate |
| bromacil | 5-bromo-6-methyl-3-(1-methylpropyl)-2,4(1H,3H)pyrimidinedione |
| bromoxynil | 3,5-dibromo-4-hydroxybenzonitrile |
| butachlor | N-(butoxymethyl)-2-chloro-N-(2,6-diethylphenyl)acetamide |
| buthidazole | 3-[5-(1,1-diemthylethyl)-1,3,4-thiadiazol-2-yl]-4-hydroxy-1-methyl-2-imidazolidinone |
| butralin | 4-(1,1-dimethylethyl)-N-(1-methylpropyl)-2,6-dinitrobenzenamine |
| butylate | S-ethyl bis(2-methylpropyl)carbamothioate |
| cacodylic acid | dimethyl arsinic oxide |
| CDAA | 2-chloro-N,N-di-2-propenylacetamide |
| CDEC | 2-chloroallyl diethyldithiocarbamate |
| CGA 142,464 | 3-(4,6-dimethoxy-1,3,5-triazin-2-yl)-1-[8 2-(2-methoxyethoxy)phenylsulfonyl]-urea |
| chloramben | 3-amino-2,5-dichlorobenzoic acid |
| chlorbromuron | 3-(4-bromo-3-chlorophenyl)-1-methoxy-1-methylurea |
| chlorimuron ethyl | 2-[[[[(4-chloro-6-methoxy-2-pyrimidinyl)ethylamino]carbonyl]amino]sulfonyl]benzoic acid, ethyl ester |
| chlormethoxynil | 2,4-dichlorophenyl 4-nitro-3-methoxyphenyl ether |
| chlornitrofen | 2,4,6-trichlorophenyl-4-nitrophenyl ether |
| chloroxuron | N'-[4-(4-chlorophenoxy)phenyl]-N,N-dimethylurea |
| chlorpropham | 1-methylethyl 3-chlorophenylcarbamate |
| chlorsulfuron | 2-chloro-N-[[(4-methoxy-6-methyl-1,3,5-triazin-2-yl)amino]carbonyl]benzenesulfonamide |
| chlortoluron | N'-(3-chloro-4-methylphenyl)-N,N-dimethylurea |
| cinmethylin | exo-1-methyl-4-(1-methylethyl)-2-[(2-methylphenyl)methoxy]-7-oxabicyclo-[2.2.1]heptane |
| clethodim | (E,E)-(±)-2-[1-[[(3-chloro-2-propenyl)oxy]imino]propyl]-5-[2-(ethylthio)propyl]-3-hydroxy-2-cyclohexen-1-one |
| clomazone | 2-[(2-chlorophenyl)methyl]-4,4-diemthyl-3-isoxazolidinone |
| cloproxydim | (E,E)-2-[1-[[(3-chloro-2-propenyl)oxy)imino]-butyl]-5-[2-(ethylthio)propyl]-3-hydroxy-2-cyclohexen-1-one |
| clopyralid | 3,6-dichloro-2-pyridinecarboxylic acid |
| CMA | calcium salt MAA |
| cyanazine | 2-[[4-chloro-6-(ethylamino)-1,3,5-triazin-2-yl]amino]-2-methylpropanenitrile |
| cycloate | S-ethyl cyclohexylethylcarbamothioate |
| cycluron | 3-cyclooctyl-1,1-dimethylurea |
| cyperquat | 1-methyl-4-phenylpyridinium |
| cyprazine | 2-chloro-4-(cyclopropylamino)-6-(isopropylamino)-s-triazine |
| cyprazole | N-[5-(2-chloro-1,1-diemthylethyl)-1,3,4-thiadiazol-2-yl]cyclopropanecarboxamide |
| cypromid | 3',4'-dichlorocyclopropanecarboxanilide |
| dalapon | 2,2-dichloropropanoic acid |
| dazomet | tetrahydro-3,5-dimethyl-2H-1,3,5-thiadiazine-2-thione |
| DCPA | dimethyl 2,3,5,6-tetrachloro-1,4-benzenedicarboxylate |
| desmediphan | ethyl [3-[[(phenylamino)carbonyl]oxy]phenyl]-carbamate |
| desmetryn | 2-(isopropylamino)-4-(methylamino)-6-(methylthio)-s-triazine |
| diallate | S-(2,3-dichloro-2-propenyl)bis(1-methylethyl)-carbamothioate |
| dicamba | 3,6-dichloro-2-methoxybenzoic acid |
| dichlobenil | 2,6-dichlorobenzonitrile |
| dichlorporp | (±)-2-(2,4-dichlorophenoxy)propanoic acid |

| Common Name | Chemical Name |
|---|---|
| dichlofop | (±)-2-[4-(2,4-dichlorophenoxy)phenoxy]propanoic acid, methyl ester |
| diethatyl | N-(chloroacetyl)-N-(2,6-diethylphenyl)glycine |
| difenzoquat | 1,2-dimethyl-3,5-diphenyl-1H-pyrazolium |
| dimepiperate | S-1-methyl-1-phenylethylpiperidine-1-carbothioate |
| dinitramine | $N^3,N^3$-diethyl-2,4-dinitro-6-(trifluoromethyl)-1,3-benzenediamine |
| dinoseb | 2-(1-methylpropyl)-4,6-dinitrophenol |
| diphenamid | N,N-dimethyl-α-phenylbenzeneacetamide |
| dipropetryn | 6-(ethylthio)-N,N'-bis(1-methylethyl)-1,3,5-triazine-2,4-diamine |
| diquat | 6,7-dihydrodipyrido[1,2-a:2',1'-c]-pyrazinedium ion |
| diuron | N'-(3,4-dichlorophenyl)-N,N-dimethylurea |
| DNOC | 2-methyl-4,6-dinitrophenol |
| DSMA | disodium salt of MAA |
| dymron | N-(4-methylphenyl)-N'-(1-methyl-1-phenylethyl)urea |
| endothall | 7-oxabicyclo[2.2.1]heptane-2,3-dicarboxylic acid |
| EPTC | S-ethyl dipropylcarbamothioate |
| esprocarb | S-benzyl-N-ethyl-N-(1,2-dimethyl)propyl)thiolcarbamate |
| ethalfluralin | N-ethyl-N-(2-methyl-2-propenyl)-2,6-dinitro-4-(trifluoromethyl)benzenamine |
| ethofumesate | (±)-2-ethoxy-2,3-dihydro-3,3-dimethyl-5-benzofuranyl methanesulfonate |
| Express ® | 2-[[[[N-(4-methoxy-6-methyl-1,3,5-triazine-2-yl)-N-methylamino]carbonyl]amino]sulfonyl]benzoic acid, methyl ester |
| fenac | 2,3,6-trichlorobenzeneacetic acid |
| fenoxaprop | (±)-2-[4-[(6-chloro-2-benzoxazolyl)oxy]phenoxy]-propanoic acid |
| fenuron | N,N-dimethyl-N'-phenylurea |
| fenuron TCA | Salt of fenuron and TCA |
| flamprop | N-benzoyl-N-(3-chloro-4-fluorophenyl)-DL-alanine |
| fluazifop | (±)-2-[4-[[5-(trifluoromethyl)-2-pyridinyl]oxy]-phenoxy]propanoic acid |
| fluazifop-P | (R)-2-[4-[[5-(trifluoromethyl)-2-pyridinyl]oxy]-phenoxy]propanoic acid |
| fluchloralin | N-(2-chloroethyl)-2,6-dinitro-N-propyl-4-(trifluoromethyl)benzenamine |
| fluometuron | N,N-dimethyl-N'-[3-(trifluoromethyl)-phenyl]urea |
| fluorochloridone | 3-chloro-4-(chloromethyl)-1-[3-(trifluoromethyl)phenyl]-2-pyrrolidinone |
| fluorodifen | p-nitrophenyl α,α,α,-trifluoro-2-nitro-p-tolyl ether |
| fluoroglycofen | carboxymethyl 5-[2-chloro-4-(trifluoromethyl)phenoxy]-2-nitrobenzoate |
| fluridone | 1-methyl-3-phenyl-5-[3-(trifluoromethyl)-phenyl]-4(1H)-pyridinone |
| fomesafen | 5-[2-chloro-4-(trifluoromethyl)phenoxy]-N-(methylsulfonyl)-2-nitrobenzamide |
| fosamine | ethyl hydrogen (aminocarbonyl)phosphate |
| glyphosate | N-(phosphonomethyl)glycine |
| haloxyfop | 2-[4-[[3-chloro-5-(trifluoromethyl)-2-pyridinyl]oxy]phenoxy]propanoic acid |
| Harmony ® | 3-[[[[(4-methoxy-6-methyl-1,3,5-triazin-2-yl)-amino]carbonyl]amino]sulfonyl]-2-thiophenecarboxylic acid, methyl ester |
| hexaflurate | potassium hexafluoroarsenate |
| hexazinone | 3-cyclohexyl-6-(dimethylamino)-1-methyl-1,3,5-triazine-2,4(1H,3H)-dione |
| imazamethabenz | 6-(4-isopropyl-4-methyl-5-oxo-2-imidazolin-2-yl)-m-toluic acid, methyl ester and 6-(4-isopropyl-4-methyl-5-oxo-2-imidazolin-2-yl)-p-toluic acid, methyl ester |
| imazapyr | (±)-2-[4,5-dihydro-4-methyl-4-(1-methylethyl)-5-oxo-1H-imidazol-2-yl]-3-pyridinecarboxylic acid |
| imazaquin | 2-[4,5-dihydro-4-methyl-4-(1-methylethyl)-5-oxo-1H-imidazol-2-yl]-3-quinolinecarboxylic acid |
| imazethapyr | (±)-2-[4,5-dihydro-4-methyl-4-(1-methylethyl)-5-oxo-1H-imidazol-2-yl]9 -5-ethyl-3-pyridinecarboxylic acid |
| ioxynil | 4-hydroxy-3,5-diiodobenzonitrile |
| isopropalin | 4-(1-methylethyl)-2,6-dinitro-N,N-dipropylbenzenamine |
| isoproturon | N-(4-isopropylphenyl)-N',N'-dimethylurea |
| isouron | N'-[5-(1,1-diemthylethyl)-3-isoxazolyl]-N,N-dimethylurea |
| isoxaben | N-[3-(1-ethyl-1-methylpropyl)-5-isoxazolyl]-2,6-dimethoxybenzamide |
| karbutilate | 3-[[(dimethylamino)carbonyl]amino]phenyl-(1,1-dimethylethyl)carbamate |
| lactofen | (±)-2-ethoxy-1-methyl-2-oxoethyl 5-[2-chloro-4-(trifluoromethyl)phenoxy]-2-nitrobenzoate |
| lenacil | 3-cyclohexyl-6,7-dihydro-1H-cyclopenta-pyrimidine-2,4(3H,5H)-dione |
| linuron | N'-(3,4-dichlorophenyl)-N-methoxy-N-methylurea |
| MAA | methylarsonic acid |
| MAMA | monoammonium salt of MAA |
| MCPA | (4-chloro-2-methylphenoxy)acetic acid |
| MCPB | 4-(4-chloro-2-methylphenoxy)butanoic acid |
| MON 7200 | S,S-dimethyl-2-(difluoromethyl)-4-(2-methylpropyl)-6-(trifluoromethyl)-3,5-pyridinedicarbothionate |
| mecoprop | (±)-2-(4-chloro-2-methylphenoxy)propanoic acid |
| mefenacet | 2-(2-benzothiazolyloxy-N-methyl-N-phenylacetamide |
| mefluidide | N-[2,4-dimethyl-5-[[(trifluoromethyl)sulfonyl]-amino]phenyl]acetamide |
| methalpropalin | N-(2-methyl-2-propenyl)-2,6-dinitro-N-propyl-4-(trifluoromethyl)benzenamide |
| methabenzthiazuron | 1,3-dimethyl-2-(2-benzothiazolyl)urea |
| metham | methylcarbamodithioic acid |
| methazole | 2-(3,4-dichlorophenyl)-4-methyl-1,2,4-oxadiazolidine-3,5-dione |
| methoxuron | N'-(3-chloro-4-methoxyphenyl)-N,N-dimethylurea |
| metolachlor | 2-chloro-N-(2-ethyl-6-methylphenyl)-N-(2-methoxy-1-methylethyl)acetamide |
| metribuzin | 4-amino-6-(1,1-dimethylethyl)-3-(methylthio)-1,2,4-triazin-5(4H)-one |
| metsulfuron methyl | 2-[[[[(4-methoxy-6-methyl-1,3,5-triazin-2-yl)-amino]carbonyl]amino]sulfonyl]benzoic acid, methyl ester |
| MH | 1,2-dihydro-3,6-pyridazinedione |
| molinate | S-ethyl hexahydro-1H-azepine-1-carbothioate |
| monolinuron | 3-(p-chlorophenyl)-1-methoxy-1-methylurea |
| monuron | N'-(4-chlorophenyl)-N,N-dimethylurea |
| monuron TCA | Salt of monuron and TCA |
| MSMA | monosodium salt of MAA |
| napropamide | N,N-diethyl-2-(1-naphthalenyloxy)propanamide |
| naptalam | 2-[(1-naphthalenylamino)carbonyl]benzoic acid |
| neburon | 1-butyl-3-(3,4-dichlorophenyl)-1-methylurea |
| nitralin | 4-(methylsulfonyl)-2,6-dinitro-N,N-dipropylaniline |
| nitrofen | 2,4-dichloro-1-(4-nitrophenoxy)benzene |
| nitrofluorfen | 2-chloro-1-(4-nitrophenoxy)-4-(trifluoromethyl)benzene |
| norea | N,N-dimethyl-N'-(octahydro-4,7-methano-1H-inden-5-yl)urea 3aa,-4a,5a,7a,7aa-isomer |
| norflurazon | 4-chloro-5-(methylamino)-2-[3-(trifluoromethyl)-phenyl]-3(2H)-pyridazinone |
| oryzalin | 4-(dipropylamino)-3,5-dinitrobenzenesulfonamide |
| oxadiazon | 3-[2,4-dichloro-5-(1-methylethoxy)phenyl]-5-(1,1-dimethylethyl)-1,3,4-oxadiazol-2(3H)-one |
| oxyfluorfen | 2-chloro-1-(3-ethoxy-4-nitrophenoxy)-4-(trifluoromethyl)benzene |
| paraquat | 1,1'-dimethyl-4,4'-dipyridinium ion |
| pebulate | S-propyl butylethylcarbamothioate |
| pendimethalin | N-(1-ethylpropyl)-3,4-dimethyl-2,6-dinitrobenzenamine |
| perfluidone | 1,1,1-trifluoro-N-[2-methyl-4-(phenylsulfonyl)-phenyl]methanesulfonamide |
| phenmedipham | 3-[(methoxycarbonyl)amino]phenyl (3-methylphenyl)carbamate |
| picloram | 4-amino-3,5,6-trichloro-2-pyridinecarboxylic acid |
| PPG-1013 | 5-[2-chloro-4-(trifluoromethyl)phenoxy]-2-nitroacetophenone oxime-O-acetic acid, methyl ester |
| pretilachlor | α-chloro-2,6-diethyl-N-(2-propoxyethyl)-acetanilide |
| procyazine | 2-[[4-chloro-6-(cyclopropylamino)-1,3,5-triazine-2-yl]amino]-2-methylpropanenitrile |
| profluralin | N-(cyclopropylmethyl)-,2,6-dinitro-N-propyl-4-(trifluoromethyl)benzenamine |
| prometon | 6-methoxy-N,N'-bis(1-methylethyl)-1,3,5- |

-continued

| Common Name | Chemical Name |
|---|---|
| | triazine-2,4-diamine |
| prometryn | N,N'-bis(1-methylethyl)-6-(methylthio)-1,3,5-triazine-2,4-diamine |
| pronamide | 3,5-dichloro-N-(1,1-dimethyl-2-propynyl)-benzamide |
| propachlor | 2-chloro-N-(1-methylethyl)-N-pehnylacetamide |
| propanil | N-(3,4-dichlorophenyl)propanamide |
| propazine | 6-chloro-N,N'-bis(1-methylethyl)-1,3,5-triazine-2,4-diamine |
| propham | 1-methylethyl phenylcarbamate |
| prosulfalin | N-[[4-(dipropylamino)-3,5-dinitrophenyl]-sulfonyl]-S,S-dimethylsulfilimine |
| prynachlor | 2-chloro-N-(1-methyl-2-propynyl)acetanilide |
| pyrazolate | 4-(2,4-dichlorobenzoyl)-1,3-dimethylpyrazol-5-yl-p-toluenesulphonate |
| pyrazon | 5-amino-4-chloro-2-phenyl-3(2H)-pyridazinone |
| pyrazosulfuron ethyl | ethyl S-[3-(4,6-dimethoxypyrimidin-2-yl)ureado-sulfonyl]-1-methylpyrazole-4-carboxylate |
| quinclorac | 3,7-dichloro-8-quinoline carboxylic acid |
| quizalofop ethyl | ($\pm$)-2-[4-[(6-chloro-2-quinoxalinyl)oxy]-phenoxy]propanoic acid, ethyl ester |
| secbumeton | N-ethyl-6-methoxy-N'-(1-methylpropyl)-1,3,5-triazine-2,4-diamine |
| sethoxydim | 2-[1-(ethoxyimino)butyl]-5-[2-(ethylthio)propyl]-3-hydroxy-2-cyclohexen-1-one |
| siduron | N-(2-methylcyclohexyl)-N'-phenylurea |
| simazine | 6-chloro-N,N'-diethyl-1,3,5-triazine-2,4-diamine |
| SK-233 | 1-($\alpha,\alpha$-dimethylbenzyl)-3-(4-methylphenyl)urea |
| sulfometuron methyl | 2-[[[[(4,6-dimethyl-2-pyrimidinyl)amino]-carbonyl]amino]sulfonyl]benzoic acid, methyl ester |
| TCA | trichloroacetic acid |
| tebuthiuron | N-[5-(1,1-dimethylethyl)-1,3,4,-thiadiazol-2-yl]-N,N'-dimethylurea |
| terbacil | 5-chloro-3-(1,1-diemthylethyl)-6-methyl-2,4(1H,3H)-pyrimidinedione |
| terbuchlor | N-(butoxymethyl)-2-chloro-N-[2-(1,1-diemthylethyl)-6-methylphenyl]acetamide |
| terbuthylazine | 2-(tert-butylamino)-4-chloro-6-(ethylamino)-s-triazine |
| terbutol | 2,6-di-tert-butyl-p-tolyl methylcarbamate |
| terbutryn | N-(1,1-dimethylethyl)-N'-ethyl-6-(methylthio)-1,3,5-triazine-2,4-diamine |
| thiobencarb | S-[(4-chlorophenyl)methyl]diethylcarbamothioate |
| triallate | S-(2,3,3-trichloro-2-propenyl) bis(1-methylethyl)-carbamothioate |
| triclopyr | [(3,5,6-trichloro-2-pyridinyl)oxy]acetic acid |
| tridiphane | 2-(3,5-dichlorophenyl)-2-(2,2,2-trichloroethyl)-oxirane |
| trifluralin | 2,6-dinitro-N,N-dipropyl-4-(trifluoromethyl)-benzenamine |
| trimeturon | 1-(p-chlorophenyl)-2,3,3-trimethylpseudourea |
| 2,4-D | (2,4-dichlorophenoxy)acetic acid |
| 2,4-DB | 4-(2,4-dichlorophenoxy)butanoic acid |
| vernolate | S-propyl dipropylcarbamothioate |
| xylachlor | 2-chloro-N-(2,3-dimethylphenyl)-N-(1-methylethyl)acetamide |

The herbicidal properties of the subject compounds were discovered in a number of greenhouse tests conducted as described below.

TABLE OF COMPOUNDS

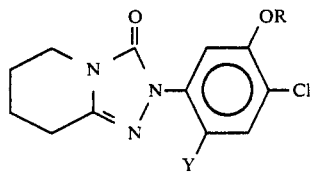

| CMPD | R | Y | m.p. (°C.) |
|---|---|---|---|
| 1 | —CH$_2$C≡CH | Cl | 167–169 |
| 2 | —CH$_2$CH=CH$_2$ | Cl | oil |

-continued

TABLE OF COMPOUNDS

| CMPD | R | Y | m.p. (°C.) |
|---|---|---|---|
| 4 | —CH(CH$_3$)$_2$ | Cl | oil |
| 5 | —CH$_2$CH=CH$_2$ | F | oil |

Compound 3 (m.p. 158–159° C.)

TEST A

Seeds of legume cover crops *Pueraria iavancia*, and *Calapogonium mucunoides* were planted in 11.4 cm square pot filled with greenhouse planting medium. *Paspalum conjugatum* cuttings were planted in 15.2 cm plastic pots filled with the same planting medium.

Plants were sprayed postemergence with the test compounds in a non-phytotoxic solvent. Treated plants were visually rated 14 days-after-treatment (DAT) and compared with the appropriate controls. The injury ratings were based on the scale of 0 to 100 where 0 indicates no effect, 20 indicates minimal effect and 100 indicates complete control. The results are shown in Table A.

TABLE A

| | | Plant Injury Rating | | |
|---|---|---|---|---|
| Compound | Rate g/ha | *Pueraria javanica* | *Calapogonium mucunoides* | *Paspalum conjugatum* |
| 1 | 250 | 80 | 90 | 30 |
| 2 | 280 | 100 | 100 | 0 |

TEST B

Rhizones of lalang (*Imperata cylindrica*) and stem cuttings of Mikania spp. were planted in separate 15.2 cm plastic pots filled with greenhouse planting medium and grown in the greenhouse. The Mikania spp. was profusely vining and the lalang had profusely growing rhizones at the time of treatment.

The plants were sprayed postemergence with the test compound in a non-phytotoxic solvent. The treatments were visually rated 24 DAT and compared with the appropriate controls. Plant injury ratings were based on the scale of 0 to 100 where 0 indicates no effect, 20 indicates minimal injury and 100 indicates complete control. The results are shown in Table B.

TABLE B

| | Rate | Plant Injury Rating | |
|---|---|---|---|
| Compound | g/ha | Mikania spp. | Lalang |

TABLE B-continued

| 1 | 250 | 70 | 0 |

TEST C

Stem cuttings of Mikania spp. and Boston fern (*Nephrolepis exaltata*) were planted in separate 15.2 cm plastic pots filled with greenhouse planting medium and grown in the greenhouse.

The plants were sprayed postemergence with the test compounds in a non-phytotoxic solvent. The treated plants were visually rated 49 DAT and compared with appropriate controls. The plant injury ratings scale used in Table A was used in this test also. The results are shown in Table C.

TABLE C

| Compound | Rate g/ha | Plant Injury Rating Mikania spp. | Boston fern |
|---|---|---|---|
| 1 | 1000 | 80 | 90 |
|   | 500 | 70 | 70 |
|   | 250 | 50 | 70 |
| 2 | 1000 | 40 | 30 |
|   | 500 | 20 | 10 |
|   | 250 | 10 | 10 |

TEST D

Loblolly pine (*Pinus taeda*), pecan (Carva spp.), Swamp oak (*Quercus* spp.), white ash (*Fraxinus americana*) and sweetgum (*Liquidambar stryaciflua*) seedlings were planted in 30-liter plastic pot filled with planting medium. The plants were grown in the greenhouse for five months before spraying.

Plants were sprayed postemergence with Compound 1 formulated in a non-phytotoxic solvent. The treated plants were visually rated 99 DAT and compared with appropriate controls. Plant injury ratings scale used in Test A was used in this test also. The results are shown in Table D.

TABLE D

| Species | Compound 1 | | | |
|---|---|---|---|---|
|   | 500 | 250 | 125 | g/ha |
| Loblolly pine | 50 | 30 | 0 |   |
| Pecan | 0 | 0 | 0 |   |
| Swamp oak | 0 | 0 | 0 |   |
| White ash | 0 | 0 | 0 |   |
| Sweet gum | 0 | 0 | 0 |   |

TEST E

Guineagrass (*Panicum maximum*) seeds elephantgrass rooted cuttings were planted in separate 15.2 cm plastic pots filled with greenhouse planting soil.

The plants were treated postemergence with Compound 1 formulated in a non-phytotoxic solvent. The guineagrass (*P. maximum*) was treated preemergence and at early and late growth stages postemergence. Treated plants were visually rated 32 DAT and compared with appropriate controls. Plant injury ratings used in Test A were also used in this test. The results are shown in Table E.

TABLE E

| | Compound 1 | | | |
|---|---|---|---|---|
|   | 500 | 250 | 125 | g/ha |
| Preemergence |   |   |   |   |
| Guineagrass | 100 | 100 | 100 |   |
| Postemergence |   |   |   |   |
| Guineagrass (early) | 100 | 100 | 30 |   |

TABLE E-continued

| | Compound 1 | | | |
|---|---|---|---|---|
|   | 500 | 250 | 125 | g/ha |
| (late) | 30 | 10 | 10 |   |
| Elephantgrass | 30 | 30 | 30 |   |

TEST F

Stem cuttings of St. Augustine grass and Alexandergrass (*Brachiaria plantagenea*), Kentucky bluegrass sod and seeds of Kentucky fescue, annual bluegrass, bermudagrass, bentgrass, large crabgrass and smooth crabgrass were planted in individual 11.4 cm square plastic pots. The plants were grown in the greenhouse until used.

The plants were sprayed postemergence with Compound 1 formulated in a non-phytotoxic solvent. The treated plants were visually rated 29 DAT compared with appropriate controls. The rating scale used in Test A was also used in this test. The results are shown in Table F.

TABLE F

| Species | Compound 1 | | | | | |
|---|---|---|---|---|---|---|
|   | 500 | 250 | 125 | 64 | 32 | g/ha |
| St. Augustine grass | 70 | 50 | 0 | 0 | 0 |   |
| Kentucky bluegrass sod | 70 | 50 | 20 | 0 | 0 |   |
| Kentucky fescue | 100 | 90 | 80 | 30 | 20 |   |
| Bermudagrass | 80 | 70 | 80 | 20 | 0 |   |
| Bentgrass | 100 | 100 | 100 | 80 | 20 |   |
| Annual bluegrass | 100 | 90 | 100 | 60 | 0 |   |
| Alexandergrass | 30 | 30 | 20 | 20 | 0 |   |
| Large crabgrass | 100 | 100 | 100 | 100 | 100 |   |
| Smooth crabgrass | 100 | 100 | 100 | 100 | 100 |   |

TEST G

Seeds of guineagrass (*P. maximum*) were planted in 15.2 cm plastic pots filled with planting medium, planting was done in two stages. Sugarcane stem cutting, paspalum (*Paspalum conjugatum*) and goldenrod (Solidago spp.) stem and rhizone cuttings were also planted in 15.2 cm plastic pots filled with planting medium. Plants were cut back often to stimulate ratoon production in the sugarcane and vigorous growth in paspalum and goldenrod.

Plants were treated postemergence with Compound 1 in a non-phytotoxic spray solvent. The treatments were visually rated 20 DAT and compared with appropriate controls. The plant injury ratings were based on the scale of 0 to 100 where 0 indicates no effect, 20 indicates minimal injury and 100 indicates complete control. The results were shown in Table G.

TABLE G

| Species | Compound 1 | | | | |
|---|---|---|---|---|---|
|   | 1000 | 500 | 250 | 125 | g/ha |
| Sugarcane | 10 | 10 | 10 | 10 |   |
| Guineagrass (early) | 100 | 100 | 100 | 100 |   |
| (late) | 80 | 70 | 20 | 10 |   |
| Goldenrod | 0 | 0 | 0 | 0 |   |
| Paspalum | 0 | 0 | 0 | 0 |   |

TEST H

Rooted cutting of rough lemon (Citrus spp.) were planted in 30-liter plastic pots and also in 11.4 cm square plastic pots. The 30-liter pots were also seeded with pigweed (*Amaranthus viridis*) sandbur (*Cenchrus echinatus*), Texas panicum (*Panicum texanum*), narrowleaf panicum (*P. maximum*) seeds and yellow nutsedge (*Cyperus esculentus*) tubers.

The citrus in the 30-liter pots were sprayed to simulate the trunk-to-trunk herbicide application method used in citrus groves, while the weeds were treated preemergence. The citrus in the 11.4 cm square pots were given direct over the top treatments. All pots were treated with Compound 1 formulated in a non-phytotoxic spray solvent. Plants were visually rated 28 DAT and compared with appropriate controls. The injury rating scale used in Test A was also used. The results are shown in Table H.

TABLE H

| | Compound 1 | | | |
|---|---|---|---|---|
| | 1000 | 500 | 250 | 125 g/ha |
| Preemergence | | | | |
| Citrus | 0 | 0 | 0 | 0 |
| Yellow nutsedge | 80 | 60 | 30 | 0 |
| Pigweed | 100 | 100 | 100 | 100 |
| Sandbur | 100 | 100 | 100 | 100 |
| Texas panicum | 100 | 100 | 100 | 100 |
| Narrowleaf panicum | 100 | 100 | 100 | 100 |
| Postemergence | 0 | 0 | 0 | 0 |
| Citrus | | | | |

TEST I

Mikania spp. vine cuttings, Boston fern (*N. exaltata*) and coffee (*Coffea* spp.) were planted separately in 15.2 cm plastic pots. Compound 1 was applied postemergence to the plants using 30 psi and 40 psi spray pressure.

In this test Compound 1 was formulated with 0.25% X-77 surfactant. Plants were visually rated 32 DAT and compared with appropriate controls. The injury rating scale used in Test A was used in this test. The results are shown in Table I.

TABLE I

| | Compound 1 | | |
|---|---|---|---|
| | 500 | 250 | 125 g/ha |
| 30 psi spray | | | |
| Mikania | 70 | 50 | 40 |
| Boston fern | 30 | 10 | 10 |
| Coffee | 0 | 0 | 0 |
| 40 psi spray | | | |
| Mikania | 80 | 70 | 40 |
| Boston fern | 90 | 60 | 20 |
| Coffee | 0 | 0 | 0 |

TEST J

Rooted rough lemon cuttings were planted in 30-liter plastic pots. The pots were also seeded with Texas panicum, guineagrass, pigweed (*A. viridis*), sandbur and yellow nutsedge tubers. Mikania spp. vine cutting and Boston fern were planted in 15.2 cm plastic pots. The plants were treated postemergence with Compound 1 formulated in non-phytotoxic spray solvent. Texas panicum, guineagrass and pigweed were seeded into the 30-liter pots and treated preemergence.

Plants were visually rated 35 DAT compared with appropriate controls. The injury ratings were based on the scale of 0 to 100 where 0 indicates no effect, 20 indicates minimal injury and 100 indicates complete control. The results are shown in Table J.

TABLE J

| | Compound 1 | | | |
|---|---|---|---|---|
| | 1000 | 500 | 250 | 125 g/ha |
| Postemergence | | | | |
| Rough lemon | 30 | 30 | 30 | 0 |
| Guineagrass | 100 | 100 | 0 | 0 |

TABLE J-continued

| | Compound 1 | | | |
|---|---|---|---|---|
| | 1000 | 500 | 250 | 125 g/ha |
| Sandbur | 100 | 100 | 100 | — |
| Pigweed | 100 | 100 | 100 | 100 |
| Texas panicum | 100 | 70 | 60 | 0 |
| Yellow nutsedge | 70 | 0 | 0 | 0 |
| Mikania | 90 | 80 | 80 | 60 |
| Boston fern | 90 | 80 | 60 | 30 |
| Preemergence | | | | |
| Texan panicum | 100 | 100 | 100 | 100 |
| Guineagrass | 100 | 100 | 100 | 100 |
| Pigweed | 100 | 100 | 100 | 100 |

TEST K

Stem cuttings of St. Augustine grass, Kentucky bluegrass sod, seeds of Kentucky fescue, bentgrass, bermudagrass, large crabgrass, smooth crabgrass, dallisgrass and blackseed plantain transplants were planted separately in 11.4 cm square pots filled with planting medium. Plants were treated postemergence with Compound 1 formulated in a non-phytotoxic spray solvent.

The treated plants were visually rated 24 DAT and compared with appropriate controls. The rating scale used in Test F was used in this test also. The results are shown in Table K. The variations in these results from those observed with Test F could be due to the fact that the tests were conducted at different times of the year.

TABLE K

| | Compound 1 | | |
|---|---|---|---|
| | 125 | 64 | 32 g/ha |
| St. Augustine grass | 30 | 30 | 30 |
| Kentucky bluegrass sod | 50 | 20 | 20 |
| Kentucky fescue | 0 | 0 | 0 |
| Bentgrass | 20 | 0 | 0 |
| Bermudagrass | 30 | 0 | 0 |
| Large crabgrass (early) | 100 | 60 | 40 |
| (late) | 40 | 0 | 0 |
| Smooth crabgrass (early) | 70 | 50 | 0 |
| (late) | 20 | 0 | 0 |
| Dallisgrass | 100 | 40 | 0 |
| Blackseed plantain | 0 | 0 | 0 |

TEST L

Plastic windowsill flats were filled with planting medium and seeded with corn, johnsongrass, shattercane, sorghum, giant foxtail, wild proso millet, large crabgrass, velvetleaf and sugarcane node cutting at the spike stage. In a second test, windowsill flats were seeded with untreated and antidote seed-treated corn, johnsongrass, velvetleaf, Williams soybean, W-20 and W-4 soybean, wild proso millet, cocklebur, untreated and antidote seed-treated sorghum, morningglory, shattercane, giant foxtail lambsquarters and sugarcane node cuttings at the spike stage.

The plants were treated preemergence with Compound 1 formulated in a non-phytotoxic spray solution. Treatments were visually rated 24 and 41 DAT and compared with appropriate controls. The injury ratings were based on the scale of 0 to 100 where 0 indicates no effect, 20 indicates minimal injury and 100 indicates complete control. The results are shown in Tables La and Lb.

TABLE La

| | Compound 1 | | |
|---|---|---|---|
| | 125 | 64 | 32 g/ha |
| Corn | 30 | 0 | 0 |

TABLE La-continued

|  | Compound 1 | | | |
| --- | --- | --- | --- | --- |
|  | 125 | 64 | 32 | g/ha |
| Johnsongrass | 100 | 80 | 70 |  |
| Shattercane | 100 | 70 | 0 |  |
| Sorghum | 100 | 0 | 0 |  |
| Giant foxtail | 100 | 100 | 100 |  |
| Wild proso millet | 100 | 90 | 70 |  |
| Large crabgrass | 100 | 100 | 100 |  |
| Velvetleaf | 100 | 100 | 100 |  |
| Sugarcane | 0 | 0 | 0 |  |

TABLE Lb

|  | Compound 1 | | | | | |
| --- | --- | --- | --- | --- | --- | --- |
|  | 500 | 250 | 125 | 65 | 32 | g/ha |
| Untreated corn | 60 | 50 | 10 | 0 | 0 |  |
| Treated corn | 0 | 0 | 0 | 0 | 0 |  |
| Johnsongrass | 100 | 100 | 80 | 60 | 60 |  |
| Velvetleaf | 100 | 100 | 100 | 100 | 100 |  |
| Williams Soybean | 100 | 100 | 80 | 30 | 20 |  |
| W-20 | 100 | 100 | 100 | 30 | 0 |  |
| W-4 | 100 | 100 | 100 | 100 | 0 |  |
| Wild proso millet | 100 | 100 | 100 | 100 | 0 |  |
| Cocklebur | 70 | 70 | 20 | 20 | 0 |  |
| Untreated Sorghum | 100 | 100 | 0 | 0 | 0 |  |
| Treated Sorghum | 100 | 100 | 0 | 0 | 0 |  |
| Morningglory | 100 | 100 | 70 | 70 | 30 |  |
| Shattercane | 100 | 100 | 50 | 50 | 20 |  |
| Giant foxtail | 100 | 100 | 100 | 100 | 80 |  |
| Lambsquarters | 100 | 100 | 100 | 100 | 100 |  |
| Sugarcane | 30 | 0 | 0 | 0 | 0 |  |

TEST M

The object of this test was to evaluate the effect of pre-plant-incorporation of Compound 1 on loblolly pine and rough lemon plants. Soil was sprayed with Compound 1. The treated soil was mixed thoroughly in plastic bags to incorporate the compound into the soil. Loblolly and rough lemon plants were then transplanted into the Compound 1 treated soil. Plants were visually rated 66 DAT and compared with the appropriate controls. The injury ratings were based on the same scale as used in Test L. The results are shown in Table M.

TABLE M

| Compound | Rate g/h | Loblolly Pine | Rough Lemon |
| --- | --- | --- | --- |
| 1 | 500 | 20 | 0 |
|  | 250 | 0 | 0 |
|  | 125 | 0 | 0 |
|  | 64 | 0 | 0 |
|  | 32 | 0 | 0 |

TEST N

Rough lemon rooted cuttings were planted in 30-liter plastic pots. The pots were also seeded with Spanish needles (*Bidens pilosa*), pigweed (*A. viridis*) narrowleaf panicum, Texas panicum, guineagrass, sandbur and purple nutsedge tubers. Mikania spp. vine cutting and Boston fern were planted in separate 15.2 cm plastic pots.

The plants were treated postemergence with Compound 1 formulated in a non-phytotoxic spray solution. The 30-liter pots were treated to simulate the trunk-to-trunk type treatment used in some citrus groves. Treatments were visually rated 37 DAT and compared with the appropriate controls. The rating scale used in Test L was used in this test also. The results are shown in Tables Na and Nb. The variations in these results from those observed for other tests could be due to the fact that the tests were conducted during different months of the year and on different growth size of plants at time of treatment. Greenhouse tests are conducted on a year-round basis (12 calendar months). These tests are repeated anytime of the year and not at the exact time when the test was first conducted.

TABLE Na

|  | Compound 1 | | | |
| --- | --- | --- | --- | --- |
|  | 1000 | 500 | 250 | g/ha |
| Rough lemon | 0 | 0 | 0 |  |
| Spanish needles | 0 | 0 | 0 |  |
| Pigweed | 100 | 100 | 100 |  |
| Narrowleaf panicum | 100 | 100 | 100 |  |
| Texas panicum | 90 | 80 | 80 |  |
| Guineagrass | 100 | 100 | 100 |  |
| Sandbur | 100 | 100 | 100 |  |
| Purple nutsedge | 0 | 0 | 0 |  |
| Mikania | 80 | 70 | 50 |  |
| Boston fern | 90 | 80 | 80 |  |

TABLE Nb

|  | Compound 1 | | | |
| --- | --- | --- | --- | --- |
|  | 1000 | 500 | 250 | g/ha |
| Rough lemon | 0 | 0 | 0 |  |
| Texas panicum | 80 | 60 | 20 |  |
| Spanish needles | 20 | 10 | 0 |  |
| Narrowleaf panicum | 90 | 80 | 10 |  |
| Pigweed | 80 | 80 | 20 |  |
| Guineagrass | 90 | 80 | 10 |  |
| Sandbur | 100 | 70 | — |  |

TEST O

Large fiberglass tubs filled with planting medium were planted with seed potato and seeded with ragweed, black nightshade, wild proso millet, giant foxtail and barnyardgrass. In another test, the tubs were planted with seed potato and volunteer pigweeds allowed to grow. The tubs were treated preemergence with Compound 1 formulated in a non-phytotoxic spray solvent. Plants were visually rated 34 and 66 DAT compared with appropriate controls. The injury ratings scale used in Test A was used in this test. The results are shown in Table Oa and Ob.

TABLE Oa

|  | Compound 1 | | |
| --- | --- | --- | --- |
|  | 250 | 125 | g/ha |
| Potato | 70 | 50 |  |
| Ragweed | 100 | 100 |  |
| Black nightshade | 100 | 100 |  |
| Wild proso millet | 100 | 100 |  |
| Giant foxtail | 100 | 100 |  |
| Barnyardgrass | 100 | 100 |  |

TABLE Ob

|  | Compound 1 | | | |
| --- | --- | --- | --- | --- |
|  | 125 | 64 | 32 | g/ha |
| Potato | 30 | 10 | 0 |  |
| Pigweed | 100 | 100 | 100 |  |

TEST P

Plastic tray liners with individual planting compartments were filled with planting medium and seeded separately with bermudagrass (*Cynodon dactylon*), broadleaf signalgrass (*Brachiaria platyphylla*), guineagrass (*Panicum maximum*), smooth crabgrass (*Digitaria ischaemum*), barnyardgrass (*Echinocloa crus-galli*), large crabgrass (*D. sanguinalis*), johnsongrass (*Sorghum hale-*

*pense*), Texas panicum (*Panicum texanum*), sandbur (*Cenchrus echinatus*), itchgrass (*Rottboellia cochichinensis*), goosegrass (*Eleusine indica*), dallisgrass (*Paspalum dilatatum*), annual bluegrass (*Poa annum*), alfalfa (*Medicago sativa*), *Pueraria javanica*, morningglory (*Ipomea* spp.), purslane (*Portulaca oleracea*), field bindweed (*Convolvulus arvensis*), ragweed (*Ambrosia elatior*), peanut (*Arachis hypogea*), purple nutsedge (*Cyperus rotundus*), yellow nutsedge (*C. esculentus*), and Kentucky bluegrass sod (*Poa pratense*). Sugarcane node cuttings were planted in 15.2 cm plastic pots filled with planting medium.

The plantings were tested peremergence and postemergence with the compounds formulated in a non-phytotoxic spray solution. Plantings were staggered so that the preemergence and postemergence treatments were sprayed on the same day. Plants were visually rated 18 to 29 days after treatment (DAT) and compared with appropriate controls. The injury ratings were based on the scale of 0 to 100 where 0 indicates no effect, 20 indicates minimal effect and 100 indicates complete control. A dash (-) indicates not determined. The variations in these results could be due to the fact that the tests were conducted at different times of the year and on plants at different growth stages. The results are shown in Tables Pa–Pr.

TABLE Pa

| | Compound 1 | | | | | | |
|---|---|---|---|---|---|---|---|
| | 1000 | 500 | 250 | 1000 | 500 | 250 | |
| | Preemergence | | | Postemergence | | | g/ha |
| Bermudagrass | 100 | 100 | 100 | 100 | 100 | 100 | |
| Broadleaf signalgrass | 100 | 100 | 100 | 100 | 100 | 100 | |
| Guineagrass | 100 | 100 | 100 | 100 | 100 | 100 | |
| Smooth crabgrass | 100 | 100 | 100 | 100 | 100 | 100 | |
| Barnyardgrass | 100 | 100 | 100 | 100 | 100 | 100 | |
| Large crabgrass | 100 | 100 | 100 | 100 | 100 | 100 | |
| Johnsongrass | 100 | 100 | 100 | 100 | 100 | 100 | |
| Texas panicum | 100 | 100 | 100 | 100 | 100 | 100 | |
| Sandbur | 100 | 100 | 100 | 100 | 100 | 100 | |
| Itchgrass | 100 | 100 | 100 | 80 | 80 | 70 | |
| Kentucky bluegrass sod | — | — | — | 60 | 50 | 20 | |
| Alfalfa | 100 | 100 | 100 | 30 | 30 | 0 | |
| *Pueraria javanica* | 100 | 100 | 100 | — | — | — | |
| Morningglory | 100 | 100 | 100 | 100 | 100 | 60 | |
| Purslane | 100 | 100 | 100 | 100 | 100 | 100 | |
| Field bindweed | 100 | 100 | 100 | 100 | 100 | 100 | |
| Ragweed | 100 | 100 | 100 | 100 | 100 | 100 | |
| Purple nutsedge | 70 | 60 | 50 | 40 | 30 | 0 | |
| Yellow nutsedge | 80 | 50 | 40 | 70 | 40 | 30 | |

TABLE Pb

| | Compound 1 | | | |
|---|---|---|---|---|
| | 32 | 16 | 8 | |
| | Postemergence | | | g/ha |
| Bermudagrass | 40 | 20 | 0 | |
| Broadleaf signalgrass | 0 | 0 | 0 | |
| Guineagrass | 0 | 0 | 0 | |
| Smooth crabgrass | 0 | 0 | 0 | |
| Large crabgrass | 0 | 0 | 0 | |
| Johnsongrass | 0 | 0 | 0 | |
| Goosegrass | 0 | 0 | 0 | |
| Yellow nutsedge | 0 | 0 | 0 | |

TABLE Pc

| | Compound 1 | | | | | | |
|---|---|---|---|---|---|---|---|
| | 500 | 250 | 125 | 500 | 250 | 125 | |
| | Preemergence | | | Postemergence | | | g/ha |
| Bermudagrass | 100 | 100 | 100 | 100 | 100 | 100 | |

TABLE Pc-continued

| | Compound 1 | | | | | | |
|---|---|---|---|---|---|---|---|
| | 500 | 250 | 125 | 500 | 250 | 125 | |
| | Preemergence | | | Postemergence | | | g/ha |
| Broadleaf signalgrass | 100 | 100 | 100 | 100 | 100 | 100 | |
| Guineagrass | 100 | 100 | 100 | 100 | 100 | 100 | |
| Smooth crabgrass | 100 | 100 | 100 | 100 | 100 | 100 | |
| Large crabgrass | 100 | 100 | 100 | 100 | 100 | 100 | |
| Johnsongrass | 100 | 100 | 100 | 100 | 100 | 100 | |
| Texas panicum | 100 | 100 | 100 | 100 | 100 | 100 | |
| Sandbur | 100 | 100 | 100 | 100 | 100 | 100 | |
| Itchgrass | 100 | 100 | 100 | 100 | 100 | 80 | |
| Dallisgrass | 100 | 100 | 100 | 100 | 100 | 100 | |
| Kentucky bluegrass sod | — | — | — | 40 | 30 | 0 | |
| Sugarcane | — | — | — | 80 | 20 | 0 | |
| Alfalfa | 100 | 100 | 100 | 100 | 100 | 100 | |
| *Pueraria javanica* | 100 | 100 | 100 | — | | | |
| Morningglory | 100 | 100 | 100 | 100 | 100 | 100 | |
| Purslane | 100 | 100 | 100 | 100 | 100 | 100 | |
| Field bindweed | 100 | 100 | 100 | 100 | 100 | 100 | |
| Ragweed | 100 | 100 | 100 | 100 | 100 | 100 | |
| Purple nutsedge | 60 | 50 | 0 | 70 | — | — | |
| Yellow nutsedge | 40 | 30 | 20 | 100 | 100 | 40 | |

TABLE Pd

| | Compound 1 | | | | | |
|---|---|---|---|---|---|---|
| | 500 | 250 | 125 | 64 | 32 | |
| | Preemergence | | | | | g/ha |
| Bermudagrass | 100 | 100 | 100 | 100 | 80 | |
| Broadleaf signalgrass | 100 | 100 | 100 | 80 | 60 | |
| Guineagrass | 100 | 100 | 100 | 100 | 100 | |
| Smooth crabgrass | 100 | 100 | 100 | 100 | 100 | |
| Large crabgrass | 100 | 100 | 100 | 100 | 100 | |
| Johnsongrass | 100 | 100 | 100 | 90 | 70 | |
| Texas panicum | 100 | 100 | 100 | 100 | 100 | |
| Sandbur | 100 | 100 | 100 | 80 | 0 | |
| Itchgrass | 100 | 100 | 100 | 60 | 40 | |
| Dallisgrass | 100 | 100 | 100 | 100 | 100 | |
| Alfalfa | 100 | 100 | 100 | 100 | 100 | |
| *Pueraria javanica* | 100 | 100 | 100 | 0 | 0 | |
| Morningglory | 100 | 100 | 100 | 80 | 60 | |
| Purslane | 100 | 100 | 100 | 100 | 100 | |
| Field bindweed | 100 | 100 | 100 | 60 | 60 | |
| Ragweed | 100 | 100 | 100 | 100 | 100 | |
| Purple nutsedge | 70 | 70 | — | 0 | 0 | |
| Yellow nutsedge | 70 | 50 | 30 | 40 | 20 | |

TABLE Pe

| | Compound 1 | | | | | |
|---|---|---|---|---|---|---|
| | 500 | 250 | 125 | 64 | 32 | |
| | Postemergence | | | | | g/ha |
| Bermudagrass | 100 | 100 | 60 | 60 | 70 | |
| Broadleaf signalgrass | 100 | 100 | 100 | 100 | 80 | |
| Guineagrass | 100 | 100 | 90 | 70 | 60 | |
| Smooth crabgrass | 100 | 100 | 80 | 50 | 70 | |
| Large crabgrass | 100 | 100 | 100 | 100 | 100 | |
| Johnsongrass | 100 | 100 | 70 | 50 | 40 | |
| Texas panicum | 100 | 100 | 90 | 90 | 0 | |
| Sandbur | 100 | 100 | 80 | 80 | 70 | |
| Itchgrass | 70 | 70 | 60 | 20 | 0 | |
| Dallisgrass | 100 | 100 | 100 | 100 | 0 | |
| Kentucky bluegrass sod | 60 | 40 | 0 | 0 | 0 | |
| Alfalfa | 70 | 40 | 0 | 50 | 0 | |
| Morningglory | 100 | 100 | 100 | 100 | 100 | |
| Purslane | 100 | 100 | 100 | 100 | 100 | |
| Field bindweed | 100 | 100 | 100 | 100 | 100 | |
| Ragweed | 100 | 100 | 100 | 100 | 100 | |
| Purple nutsedge | 60 | 50 | 30 | 0 | 0 | |
| Yellow nutsedge | 90 | 70 | 30 | 0 | 0 | |

TABLE Pf

| | Compound 1 | | | | | | |
|---|---|---|---|---|---|---|---|
| | 500 | 250 | 125 | 500 | 250 | 125 | |
| | Preemergence | | | Postemergence | | | g/ha |
| Bermudagrass | 100 | 100 | 100 | 100 | 100 | 0 | |
| Broadleaf signalgrass | 100 | 100 | 100 | 100 | 100 | 70 | |
| Guineagrass | 100 | 100 | 100 | 100 | 100 | 60 | |
| Smooth crabgrass | 100 | 100 | 100 | 100 | 100 | 50 | |
| Large crabgrass | 100 | 100 | 100 | 100 | 100 | 20 | |
| Johnsongrass | 100 | 100 | 100 | 70 | 70 | 40 | |
| Texas panicum | 100 | 100 | 100 | 100 | 100 | 70 | |
| Itchgrass | 100 | 100 | 100 | 70 | 70 | 50 | |
| Goosegrass | 100 | 100 | 100 | — | — | — | |
| Dallisgrass | 100 | 100 | 100 | 100 | 100 | 100 | |
| Kentucky bluegrass sod | — | — | — | 30 | 30 | 0 | |
| Sugarcane | | | | | | | |
| Alfalfa | 100 | 100 | 100 | 50 | 40 | 0 | |
| Pueraria javanica | 100 | 100 | 100 | — | — | — | |
| Morningglory | 100 | 100 | 100 | 100 | 100 | 40 | |
| Purslane | 100 | 100 | 100 | 100 | 100 | 100 | |
| Field bindweed | — | — | — | 100 | 100 | 100 | |
| Ragweed | 100 | 100 | 100 | 100 | 100 | 80 | |
| Purple nutsedge | 50 | 0 | 0 | 60 | 0 | 0 | |
| Yellow nutsedge | 60 | 60 | 0 | 60 | 50 | 0 | |

TABLE Pg

| | Compound 1 | | | | | | |
|---|---|---|---|---|---|---|---|
| | 500 | 250 | 125 | 500 | 250 | 125 | |
| | Preemergence | | | Postemergence | | | g/ha |
| Bermudagrass | 100 | 100 | 100 | 100 | 100 | 80 | |
| Broadleaf signalgrass | 100 | 100 | 100 | 100 | 100 | 100 | |
| Guineagrass | 100 | 100 | 100 | 100 | 100 | 100 | |
| Smooth crabgrass | 100 | 100 | 100 | 100 | 100 | 70 | |
| Large crabgrass | 100 | 100 | 100 | 100 | 100 | 90 | |
| Johnsongrass | 100 | 100 | 100 | 100 | 100 | 100 | |
| Texas panicum | 100 | 100 | 100 | 100 | 100 | 100 | |
| Sandbur | 100 | 100 | 90 | — | — | — | |
| Itchgrass | 100 | 100 | 90 | 100 | 90 | 80 | |
| Goosegrass | 100 | 100 | 100 | 100 | 100 | 100 | |
| Dallisgrass | 100 | 100 | 100 | 100 | 100 | 100 | |
| Annual bluegrass | 100 | 100 | 80 | 100 | 100 | 100 | |
| Kentucky bluegrass sod | — | — | — | 90 | 30 | 20 | |
| Sugarcane | — | — | — | 50 | 10 | 0 | |
| Alfalfa | 100 | 80 | 80 | 80 | 70 | 10 | |
| Pueraria javanica | 100 | 90 | 70 | — | — | — | |
| Morningglory | 100 | 70 | 30 | 100 | 90 | 80 | |
| Purslane | 100 | 100 | 100 | 100 | 100 | 100 | |
| Ragweed | 100 | 100 | 100 | 100 | 100 | 90 | |
| Peanut | 70 | 80 | 50 | 90 | 60 | 30 | |
| Purple nutsedge | — | — | — | 30 | 10 | 10 | |
| Yellow nutsedge | — | — | — | 50 | 20 | 0 | |

TABLE Ph

| | Compound 1 | | |
|---|---|---|---|
| | 250 Preemergence | 250 Postemergence | g/ha |
| Bermudagrass | 100 | 100 | |
| Broadleaf signalgrass | 100 | 100 | |
| Guineagrass | 100 | 100 | |
| Smooth crabgrass | 100 | 90 | |
| Large crabgrass | 100 | 90 | |
| Johnsongrass | 100 | 100 | |
| Texas panicum | 100 | 100 | |
| Sandbur | 80 | 100 | |
| Itchgrass | 90 | 90 | |
| Goosegrass | 100 | 100 | |
| Dallisgrass | 100 | 100 | |
| Annual bluegrass | 70 | 100 | |
| Kentucky bluegrass sod | — | 10 | |
| Alfalfa | 50 | 20 | |
| Pueraria javanica | 20 | — | |
| Morningglory | 0 | 80 | |
| Purslane | 100 | 90 | |
| Ragweed | 20 | 100 | |
| Peanut | 20 | 70 | |
| Purple nutsedge | — | 10 | |
| Yellow nutsedge | — | 80 | |

TABLE Pi

| | Compound 1 | | |
|---|---|---|---|
| | 250 Preemergence | 250 Postemergence | g/ha |
| Bermudagrass | 100 | 80 | |
| Broadleaf signalgrass | 100 | 40 | |
| Guineagrass | 100 | 30 | |
| Smooth crabgrass | 100 | 20 | |
| Large crabgrass | 100 | 80 | |
| Johnsongrass | 100 | 100 | |
| Texas panicum | 100 | 100 | |
| Sandbur | 100 | 80 | |
| Itchgrass | 90 | 100 | |
| Goosegrass | — | 40 | |
| Dallisgrass | 100 | 50 | |
| Annual bluegrass | 0 | 10 | |
| Kentucky bluegrass sod | — | 0 | |
| Alfalfa | 90 | 60 | |
| Pueraria javanica | 30 | — | |
| Morningglory | 100 | 100 | |
| Purslane | 100 | 100 | |
| Ragweed | 100 | 100 | |
| Peanut | 10 | 50 | |
| Purple nutsedge | — | 60 | |
| Yellow nutsedge | — | 90 | |

TABLE Pj

| | Compound 2 | | | | | | |
|---|---|---|---|---|---|---|---|
| | 1000 | 500 | 250 | 1000 | 500 | 250 | |
| | Preemergence | | | Postemergence | | | g/ha |
| Bermudagrass | 100 | 100 | 100 | 100 | 100 | 40 | |
| Broadleaf signalgrass | 100 | 100 | 100 | 100 | 100 | 40 | |
| Guineagrass | 100 | 100 | 100 | 100 | 100 | 30 | |
| Smooth crabgrass | 100 | 100 | 100 | 100 | 100 | 60 | |
| Barnyardgrass | 100 | 100 | 100 | 100 | 100 | 40 | |
| Large crabgrass | 100 | 100 | 100 | 100 | 100 | 80 | |
| Johnsongrass | 100 | 100 | 100 | 100 | 60 | 30 | |
| Texas panicum | 100 | 100 | 100 | 100 | 100 | 60 | |
| Sandbur | 100 | 100 | 100 | 100 | 100 | 40 | |
| Itchgrass | 100 | 100 | 100 | 70 | 50 | 0 | |
| Kentucky bluegrass sod | — | — | — | 60 | 30 | 0 | |
| Alfalfa | 100 | 100 | 100 | 100 | 50 | 50 | |
| Pueraria javanica | 100 | 100 | 100 | — | — | — | |
| Morningglory | 100 | 100 | 60 | 100 | 100 | 30 | |
| Purslane | 100 | 100 | 100 | 100 | 100 | 100 | |
| Field bindweed | 100 | 100 | 100 | 100 | 100 | 100 | |
| Ragweed | 100 | 100 | 70 | 70 | 60 | 0 | |
| Purple nutsedge | 60 | 50 | 0 | 20 | 0 | 0 | |
| Yellow nutsedge | 60 | 30 | 0 | 60 | 30 | 0 | |

TABLE Pk

| | Compound 2 | | | | | | |
|---|---|---|---|---|---|---|---|
| | 500 | 250 | 125 | 500 | 250 | 125 | |
| | Preemergence | | | Postemergence | | | g/ha |
| Bermudagrass | 100 | 100 | 100 | 10 | 90 | 0 | |
| Broadleaf signalgrass | 100 | 100 | 100 | 100 | 70 | 0 | |
| Guineagrass | 100 | 100 | 100 | 90 | 0 | 0 | |
| Smooth crabgrass | 100 | 100 | 90 | 0 | 0 | 0 | |
| Large crabgrass | 100 | 100 | 80 | 80 | 20 | 0 | |
| Johnsongrass | 100 | 40 | 50 | 100 | 40 | 0 | |
| Texas panicum | 100 | 100 | 70 | 100 | 70 | 0 | |
| Sandbur | 100 | 100 | 100 | — | — | — | |

TABLE Pk-continued

| | Compound 2 | | | | | | |
|---|---|---|---|---|---|---|---|
| | 500 | 250 | 125 | 500 | 250 | 125 | |
| | Preemergence | | | Postemergence | | | g/ha |
| Itchgrass | 100 | 70 | 30 | 50 | 10 | 0 | |
| Goosegrass | 100 | 100 | 100 | 100 | 80 | 0 | |
| Dallisgrass | 100 | 100 | 80 | 90 | 20 | 0 | |
| Annual bluegrass | 60 | 20 | 0 | 70 | 30 | 0 | |
| Kentucky bluesod | — | — | — | 20 | 0 | 10 | |
| Sugarcane | — | — | — | 0 | 0 | 0 | |
| Alfalfa | 70 | 30 | 0 | 20 | 20 | 0 | |
| *Pueraria javanica* | 50 | 20 | 0 | — | — | — | |
| Morningglory | 70 | 10 | 10 | 100 | 90 | 20 | |
| Purslane | 100 | 100 | 100 | 100 | 100 | 80 | |
| Ragweed | 100 | 30 | 20 | 80 | 80 | 10 | |
| Peanut | 40 | 30 | 10 | 60 | 10 | 0 | |
| Purple nutsedge | — | — | — | 10 | 0 | 0 | |
| Yellow nutsedge | — | — | — | 60 | 0 | 0 | |

TABLE Pl

| | Compound 2 | | |
|---|---|---|---|
| | 250 | 250 | |
| | Preemergence | Postemergence | g/ha |
| Bermudagrass | 100 | 0 | |
| Broadleaf signalgrass | 90 | 20 | |
| Guineagrass | 100 | 30 | |
| Smooth crabgrass | 100 | 0 | |
| Large crabgrass | 60 | 10 | |
| Johnsongrass | 20 | 10 | |
| Texas panicum | 100 | 30 | |
| Sandbur | 10 | 0 | |
| Itchgrass | 40 | 0 | |
| Goosegrass | 100 | 80 | |
| Dallisgrass | 90 | 10 | |
| Annual bluegrass | 0 | 0 | |
| Kentucky bluegrass sod | — | 0 | |
| Alfalfa | 0 | 20 | |
| *Pueraria javanica* | 0 | | |
| Morningglory | 0 | 20 | |
| Purslane | 100 | 60 | |
| Ragweed | 40 | 10 | |
| Peanut | 0 | 20 | |
| Purple nutsedge | — | 0 | |
| Yellow nutsedge | — | 0 | |

TABLE Pm

| | Compound 5 | | | | | | |
|---|---|---|---|---|---|---|---|
| | 500 | 250 | 125 | 500 | 250 | 125 | |
| | Preemergence | | | Postemergence | | | g/ha |
| Bermudagrass | 100 | 100 | 0 | 100 | 0 | 0 | |
| Broadleaf signalgrass | 100 | 90 | 90 | 100 | 60 | 0 | |
| Guineagrass | 100 | 100 | 100 | 100 | 0 | 0 | |
| Smooth crabgrass | 100 | 100 | 100 | 20 | 0 | 0 | |
| Large crabgrass | 100 | 100 | 100 | 60 | 30 | 0 | |
| Johnsongrass | 90 | 80 | 80 | 100 | 80 | 20 | |
| Texas panicum | 100 | 100 | 100 | 100 | 80 | 0 | |
| Sandbur | 40 | 40 | 20 | — | — | — | |
| Itchgrass | 70 | 60 | 30 | 40 | 0 | 10 | |
| Goosegrass | 100 | 100 | 100 | 100 | 20 | 30 | |
| Dallisgrass | 100 | 90 | 70 | 90 | 90 | 10 | |
| Annual bluegrass | 60 | 10 | 10 | 100 | 20 | 0 | |
| Kentucky bluegrass sod | — | — | — | 0 | 0 | 0 | |
| Sugarcane | — | — | — | 0 | 0 | 0 | |
| Alfalfa | 0 | 20 | 0 | 50 | 50 | 0 | |
| *Pueraria javanica* | 90 | 10 | 0 | — | — | — | |
| Morningglory | 90 | 20 | 10 | 100 | 100 | 100 | |
| Purslane | 100 | 100 | 100 | 100 | 100 | 100 | |
| Ragweed | 100 | 80 | 90 | 100 | — | 60 | |
| Peanut | 40 | 30 | 20 | 60 | 50 | 20 | |
| Purple nutsedge | — | — | — | 10 | 0 | 0 | |
| Yellow nutsedge | — | — | — | 30 | 20 | 20 | |

TABLE Pn

| | Compound 3 | | |
|---|---|---|---|
| | 125 | 125 | |
| | Preemergence | Postemergence | g/ha |
| Bermudagrass | 100 | 0 | |
| Broadleaf signalgrass | 70 | 20 | |
| Guineagrass | 100 | 20 | |
| Smooth crabgrass | 100 | 0 | |
| Large crabgrass | 100 | 0 | |
| Johnsongrass | 100 | 0 | |
| Texas panicum | 100 | 90 | |
| Itchgrass | 60 | 30 | |
| Goosegrass | 100 | — | |
| Dallisgrass | — | 0 | |
| Kentucky bluegrass sod | — | 0 | |
| Alfalfa | 100 | 70 | |
| *Pueraria javanica* | 0 | — | |
| Morningglory | 100 | 100 | |
| Purslane | 100 | 100 | |
| Field bindweed | — | 100 | |
| Ragweed | 100 | 100 | |
| Purple nutsedge | 0 | 0 | |
| Yellow nutsedge | 0 | 0 | |

TABLE Po

| | Compound 3 | | |
|---|---|---|---|
| | 125 | 125 | |
| | Preemergence | Postemergence | g/ha |
| Bermudagrass | 100 | 0 | |
| Broadleaf signalgrass | 100 | 100 | |
| Guineagrass | 100 | 10 | |
| Smooth crabgrass | 100 | 0 | |
| Large crabgrass | 100 | 50 | |
| Johnsongrass | 100 | 100 | |
| Texas panicum | 100 | 100 | |
| Sandbur | 90 | — | |
| Itchgrass | 90 | 30 | |
| Goosegrass | 100 | 100 | |
| Dallisgrass | 100 | 90 | |
| Annual bluegrass | 80 | 80 | |
| Kentucky bluegrass sod | — | 0 | |
| Sugarcane | — | 0 | |
| Alfalfa | 100 | 60 | |
| *Pueraria javanica* | 80 | — | |
| Morningglory | 60 | 100 | |
| Purslane | 100 | 100 | |
| Ragweed | 100 | 100 | |
| Peanut | 70 | 70 | |
| Purple nutsedge | — | 0 | |
| Yellow nutsedge | — | 10 | |

TABLE Pp

| | Compound 3 | | | | | |
|---|---|---|---|---|---|---|
| | 125 | 64 | 32 | 16 | 4 | |
| | Preemergence | | | | | g/ha |
| Bermudagrass | 100 | 100 | 100 | 100 | 20 | |
| Broadleaf signalgrass | 100 | 100 | 100 | 60 | 20 | |
| Guineagrass | 100 | 100 | 100 | 100 | 30 | |
| Smooth crabgrass | 100 | 100 | 100 | 100 | 50 | |
| Large crabgrass | 100 | 100 | 100 | 95 | 60 | |
| Johnsongrass | 100 | 100 | 100 | 85 | 30 | |
| Texas panicum | 100 | 100 | 95 | 95 | 30 | |
| Itchgrass | 100 | 100 | 100 | 95 | 60 | |
| Alfalfa | 100 | 100 | 100 | 100 | 40 | |
| *Pueraria javanica* | 100 | 100 | 90 | 80 | 50 | |
| Morningglory | 100 | 100 | 80 | 90 | 40 | |
| Purslane | 100 | 100 | 100 | 100 | 100 | |
| Field bindweed | 100 | 100 | 100 | 100 | 100 | |
| Ragweed | 100 | 100 | 100 | 100 | 0 | |
| Purple nutsedge | 100 | 100 | 100 | 60 | 30 | |
| Yellow nutsedge | 100 | 100 | 90 | 60 | 40 | |

TABLE Pq

| | Compound 3 | | | | | |
|---|---|---|---|---|---|---|
| | 125 | 64 | 32 | 16 | 4 | |
| | Postemergence | | | | | g/ha |
| Bermudagrass | 100 | 100 | 95 | 80 | 50 | |
| Broadleaf signalgrass | 100 | 100 | 100 | 50 | 20 | |
| Guineagrass | 100 | 100 | 100 | 50 | 20 | |
| Smooth crabgrass | 100 | 100 | 80 | 70 | 20 | |
| Large crabgrass | 100 | 100 | 100 | 95 | 40 | |
| Johnsongrass | 100 | 100 | 100 | 100 | 20 | |
| Texas panicum | 100 | 100 | 95 | 80 | 20 | |
| Itchgrass | 100 | 100 | 80 | 60 | 30 | |
| Kentucky bluegrass sod | 85 | 60 | 30 | 30 | 20 | |
| Alfalfa | 100 | 100 | 95 | 95 | 40 | |
| Morningglory | 100 | 100 | 100 | 100 | 50 | |
| Purslane | 100 | 100 | 100 | 100 | 100 | |
| Field bindweed | 100 | 100 | 100 | 100 | 100 | |
| Ragweed | 100 | 100 | 90 | 80 | 20 | |
| Purple nutsedge | 100 | 100 | 60 | 40 | 30 | |
| Yellow nutsedge | 100 | 100 | 90 | 60 | 20 | |

TABLE Pr

| | Compound 4 | | |
|---|---|---|---|
| | 250 | 250 | |
| | Preemergence | Postemergence | g/ha |
| Bermudagrass | 90 | 0 | |
| Broadleaf signalgrass | 100 | 20 | |
| Guineagrass | 100 | 30 | |
| Smooth crabgrass | 100 | 0 | |
| Large crabgrass | 100 | 0 | |
| Johnsongrass | 100 | 30 | |
| Texas panicum | 100 | 10 | |
| Sandbur | 0 | 70 | |
| Itchgrass | 0 | 0 | |
| Goosegrass | 100 | 50 | |
| Dallisgrass | 100 | 80 | |
| Annual bluegrass | 60 | 0 | |
| Kentucky bluegrass sod | — | 0 | |
| Alfalfa | 0 | 10 | |
| *Pueraria javanica* | 30 | — | |
| Morningglory | 0 | 40 | |
| Purslane | 100 | 50 | |
| Ragweed | 100 | 20 | |
| Peanut | 20 | 20 | |
| Purple nutsedge | — | 10 | |
| Yellow nutsedge | — | 30 | |

TEST Q

Seeds of crabgrass (Digitaria spp.), barnyardgrass (*Echinochloa crus-galli*), giant foxtail (*Setaria faberi*), wild oats (*Avena fatua*), cheatgrass (*Bromus secalinus*), velvetleaf (*Abutilon theophrasti*), morningglory (Ipomoea spp.), cocklebur (*Xanthium pensylvanicum*), sorghum, corn, soybean, sugarbeet, cotton, rice, wheat, barley, cassia and purple nutsedge (*Cyperus rotundus*) tubers were planted and treated preemergence with the test chemicals dissolved in a non-phytotoxic solvent. At the same time, these crops and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Tables Qa–Qg are based on a numerical scale extending from 0=no injury, to 10=complete kill. The accompanying descriptive symbols have the following meanings:

C=chlorosis/necrosis
B=burn
D=defoliation
E=emergence inhibition
G=growth retardation
H=formative effect
U=unusual pigmentation
X=axillary stimulation
S=albinism
6Y=abscised buds or flowers

TABLE Qa

| | Compound 1 | | | | |
|---|---|---|---|---|---|
| | 2000 | 400 | 2000 | 400 | |
| | Preemergence | | Postemergence | | g/ha |
| Corn | 10C | 9H | 9B | 9B | |
| Soybean | 10C | 10C | 10B | 10B | |
| Cotton | | | 10B | 10B | |
| Sorghum | 10C | 10C | 10B | 10B | |
| Morningglory | 10C | 10C | 10B | 10B | |
| Crabgrass | 10C | 10C | 10B | 10B | |
| Rice | 10C | 10C | 10B | 10B | |
| Barnyardgrass | 10C | 10C | 10B | 10B | |
| Spring wheat | 10C | 10C | 10B | 10B | |
| Wild oats | 10C | 10C | 10B | 10B | |
| Nutsedge | 10C | 10C | 10B | 9B | |
| Cocklebur | 10C | 10C | 10B | 10B | |
| Cassia | 10C | 10C | 10B | 10B | |

TABLE Qb

| | Compound 1 | | | | |
|---|---|---|---|---|---|
| | 50 | 10 | 50 | 10 | |
| | Preemergence | | Postemergence | | g/ha |
| Corn | 4C,9H | 3C,8H | 9B | 4B | |
| Soybean | 2C,9G | 9G | 9B | 9B | |
| Cotton | 10C | 3G | 10B | 10B | |
| Sorghum | 9C | 9C | 8B | 5B | |
| Velvetleaf | 10C | 10C | 10B | 9B | |
| Morningglory | 10C | 2C,8H | 10B | 9B | |
| Giant foxtail | 10H | 9H | 9B | 7B | |
| Crabgrass | 10H | | 6B | 5B | |
| Rice | 9C | 2C,3G | 9B | 6B | |
| Barnyardgrass | 9H | 9H | 10B | 3B | |
| Spring wheat | 9C | 2C | 8B | 5B | |
| Winter barley | 9C | 8C | 9B | 5B | |
| Sugarbeet | 10G | 8G | 10B | 9B | |
| Wild oats | 8C | 1C | 8B | 6B | |
| Nutsedge | 7G | 3G | 8B | 7B | |
| Cheatgrass | 5G | 0 | 7B | 5B | |
| Cocklebur | 8C | 1H | 7B | 7B | |

TABLE Qc

| | Compound 2 | | |
|---|---|---|---|
| | 400 | 400 | |
| | Preemergence | Postemergence | g/ha |
| Corn | 9H | 8B | |
| Soybean | 10H | 10B | |
| Cotton | | 10B | |
| Sorghum | 10C | 10B | |
| Morningglory | 10C | 10B | |
| Crabgrass | 10C | 10B | |
| Rice | 10C | 10B | |
| Barnyardgrass | 10C | 10B | |
| Spring wheat | 10C | 9B | |
| Wild oats | 10C | 10B | |
| Nutsedge | 10C | 9B | |
| Cocklebur | 10C | 10B | |
| Cassia | 10C | 9B | |

TABLE Qd

| | Compound 3 | | | | | | |
|---|---|---|---|---|---|---|---|
| | 400 | 50 | 10 | 400 | 50 | 10 | |
| | Preemergence | | | Postemergence | | | g/ha |
| Corn | 10H | 4C,9H | 3C,8H | 10B | 9B | 7B | |
| Soybean | 10E | 2C,9G | 8G | 10B | 9B | 8B | |
| Cotton | 10H | 6H | 2G | 10B | 10B | 10B | |
| Sorghum | 10H | 9H | 8H | 10B | 9B | 7B | |
| Velvetleaf | 10H | 10H | 10H | 10B | 10B | 10B | |
| Morningglory | 10H | 9H | 2C,8H | 10B | 10B | 9B | |
| Giant foxtail | 10H | 10H | 9H | 10B | 10B | 9B | |

TABLE Qd-continued

| | Compound 3 | | | | | | |
|---|---|---|---|---|---|---|---|
| | 400 | 50 | 10 | 400 | 50 | 10 | |
| | Preemergence | | | Postemergence | | | g/ha |
| Crabgrass | 10E | 10H | 9H | 10B | 10B | 7B | |
| Rice | 10H | 3C,7G | 2C,7G | 10B | 9B | 7B | |
| Barnyardgrass | 10H | 10H | 5C,8H | 10B | 10B | 8B | |
| Spring wheat | 10H | 2C,7H | 3C,6G | 10B | 8B | 6B | |
| Winter barley | 10H | 5C,9H | 6C | 10B | 8B | 6B | |
| Sugarbeet | 10H | 10H | 7H | 10B | 10B | 9B | |
| Wild oats | 9H | 3C,6H | 2C | 10B | 9B | 7B | |
| Nutsedge | 10C | — | — | 10B | 9B | 4B | |
| Cheatgrass | 9H | 5G | 0 | 10B | 9B | 4B | |
| Cocklebur | 10H | 3C,6G | 2C | 10B | 8B | 7B | |

TABLE Qe

| | Compound 4 | | |
|---|---|---|---|
| | 400 | 400 | |
| | Preemergence | Postemergence | g/ha |
| Corn | 8B | 8B | |
| Soybean | 9C | 9B | |
| Cotton | — | 10B | |
| Sorghum | 10C | 9B | |
| Morningglory | 10C | 10B | |
| Crabgrass | 10C | 10B | |
| Rice | 10C | 10B | |
| Barnyardgrass | 10C | 10B | |
| Spring wheat | 10C | 9B | |
| Wild oats | 10C | 10B | |
| Nutsedge | 10C | 9B | |
| Cocklebur | 10C | 9B | |
| Cassia | 10C | 10B | |

TABLE Qf

| | Compound 4 | | | | |
|---|---|---|---|---|---|
| | 50 | 10 | 50 | 10 | |
| | Preemergence | | Postemergence | | g/ha |
| Corn | 2C,7H | 0 | 3B | 3B | |
| Soybean | 2C,8G | 3G | 5B | 7B | |
| Cotton | 2C,3G | 0 | 10B | 10B | |
| Sorghum | 8C | 3C | 6B | 4B | |
| Velvetleaf | 10C | 10C | 10B | 4B | |
| Morningglory | 1C,3G | 2C,4G | 9B | 5B | |
| Giant foxtail | 8H | 3C | 7B | 3B | |
| Crabgrass | 10E | 7G | 6B | 1C | |
| Rice | 7C | 0 | 8B | 3B | |
| Barnyardgrass | 9C | 7C | 8B | 3B | |
| Spring wheat | 4C,6G | 2G | 7B | 3B | |
| Winter barley | 8C | 2C | 5B | 3B | |
| Sugarbeet | 8G | 4G | 7B | 3B | |
| Wild oats | 3C,6G | 2G | 7B | 3B | |
| Nutsedge | 4C | 0 | 6B | 1B | |
| Cheatgrass | 5G | 0 | 4B | 1B | |
| Cocklebur | 0 | 0 | 6B | 4B | |

TABLE Qg

| | Compound 5 | | | | |
|---|---|---|---|---|---|
| | 50 | 10 | 50 | 10 | |
| | Preemergence | | Postemergence | | g/ha |
| Corn | 5G | 3G | 7B | 3B | |
| Soybean | 9G | 0 | 9B | 7B | |
| Cotton | 3C,7G | 1C | 10B | 9B | |
| Sorghum | 3C,5G | 0 | 9B | 5B | |
| Velvetleaf | 10C | 9C | 10B | 10B | |
| Morningglory | 9H | 0 | 10B | 9B | |
| Giant foxtail | 9H | 5H | 9B | 8B | |
| Crabgrass | 8H | 0 | 9B | 6B | |
| Rice | 3G | 0 | 9B | 6B | |
| Barnyardgrass | 3C,9H | 3C,8H | 10B | 7B | |
| Spring wheat | 7C | 2C | 6B | 4B | |
| Winter barley | 3G | 1C,5G | 7B | 4B | |
| Sugarbeet | 9C | 8H | 9B | 8B | |
| Wild oats | 4C | 0 | 10B | 5B | |
| Nutsedge | 3G | — | 5B | 2B | |

TABLE Qg-continued

| | Compound 5 | | | | |
|---|---|---|---|---|---|
| | 50 | 10 | 50 | 10 | |
| | Preemergence | | Postemergence | | g/ha |
| Cheatgrass | 2G | 0 | 7B | 2B | |
| Cocklebur | 6H | 0 | 8B | 7B | |

TEST R

Postemergence

Three round pans (25 cm diameter by 12.5 cm deep) were filled with Sassafras sandy loam soil. One pan was planted with nutsedge (*Cyperus rotundus*) tubers, crabgrass (*Digitaria sanguinalis*), sicklepod, (*Cassia obtusifolia*), jimsonweed (*Datura stramonium*), velvetleaf (*Abutilon theophrasti*), lambsquarters (*Chenopodium album*), rice (*Oryza sativa*), and teaweed (*Sida spinosa*). The second pot was planted with green foxtail (*Setaria viridis*), cocklebur (*Xanthium pensylvanicum*), morningglory (*Ipomoea hederacea*), cotton (*Gossypium hirsutum*), johnsongrass (*Sorghum halepense*), barnyardgrass (*Echinochloa crus-galli*), corn (*Zea mays*), soybean (*Glycine max*), and giant foxtail (*Setaria faberi*). The third pot was planted with wheat (*Triticum aestivum*), barley (*Hordeum vulgare*), wild buckwheat (*Polygonum convolvulus*), downy brome (*Bromus tectorum*), sugarbeet (*Beta vulgaris*), wild oat (*Avena fatua*), common chickweed (*Stellaria media*), blackgrass (*Alopecurus myosuroides*), and rape (*Brassica napus*). The plants were grown for approximately fourteen days, then sprayed postemergence with the chemicals dissolved in a non-phytotoxic solvent.

Preemergence

Three round pans (25 cm diameter by 12.5 cm deep) were filled with Sassafras sandy loam soil. One pan was planted with nutsedge tubers, crabgrass, sicklepod, jimsonweed, velvetleaf, lambsquarters, rice, and teaweed. The second pot was planted with green foxtail, cocklebur, morningglory, cotton, johnsongrass, barnyardgrass, corn, soybean, and giant foxtail. The third pot was planted with wheat, barley, wild buckwheat, downy brome, sugarbeet, wild oat, common chickweed, blackgrass, and rape. The three pans were sprayed preemergence with the chemicals dissolved in a non-phytotoxic solvent.

Treated plants and controls were maintained in the greenhouse for approximately 24 days, then all rated plants were compared to controls and visually rated for plant response.

Response ratings used in Test Q were used in some tests. In other tests the ratings are based on a scale of 0 to 100 where 0 indicates no effect, 20 minimal injury and 100 indicated complete control. A dash (-) response means no test was conducted. The results are shown in Tables Ra through Re.

TABLE Ra

| | Compound 1 | | | | |
|---|---|---|---|---|---|
| | 125 | 62 | 16 | 4 | |
| | Preemergence | | | | g/ha |
| Spring wheat | 30 | 0 | 0 | 0 | |
| Sugarbeet | 100 | 100 | 100 | 70 | |
| Rape | 100 | 100 | 60 | 30 | |
| Wild oats | 100 | 60 | 30 | 0 | |
| Blackgrass | 100 | 80 | 50 | 30 | |
| Rice | 100 | 60 | 30 | 0 | |
| Lambsquarters | 100 | 100 | 100 | 100 | |
| Wild buckwheat | 100 | 100 | 100 | 100 | |
| Chickweed | 100 | 80 | 50 | 30 | |
| Corn | 0 | 0 | 0 | 0 | |

TABLE Ra-continued

| | Compound 1 | | | | |
|---|---|---|---|---|---|
| | 125 | 62 | 16 | 4 | |
| | Preemergence | | | | g/ha |
| Soybean | 100 | 60 | 20 | 0 | |
| Cotton | 70 | 40 | 20 | 0 | |
| Velvetleaf | 100 | 100 | 70 | 50 | |
| Morningglory | 100 | 100 | 60 | 30 | |
| Crabgrass | 100 | 100 | 100 | 90 | |
| Giant foxtail | 100 | 100 | 100 | 100 | |
| Barnyardgrass | 100 | 100 | 50 | 30 | |
| Johnsongrass | 100 | 100 | 60 | 30 | |
| Nutsedge | 50 | 30 | 0 | 0 | |
| Green foxtail | 100 | 100 | 100 | 70 | |
| Cocklebur | 90 | 60 | 30 | 0 | |
| Teaweed | 100 | 100 | 90 | 70 | |
| Cassia | 100 | 100 | 70 | 30 | |
| Jimsonweed | 100 | 100 | 100 | 90 | |
| Cheatgrass | 90 | 60 | 30 | 0 | |

TABLE Rb

| | Compound 1 | | | | |
|---|---|---|---|---|---|
| | 125 | 62 | 16 | 4 | |
| | Postemergence | | | | g/ha |
| Spring wheat | 90 | 80 | 40 | 30 | |
| Sugarbeet | 100 | 100 | 90 | 60 | |
| Rape | 100 | 100 | 80 | 30 | |
| Wild oats | 90 | 90 | 60 | 20 | |
| Blackgrass | 90 | 90 | 40 | 30 | |
| Lambsquarters | 100 | 100 | 100 | 100 | |
| Wild buckwheat | 100 | 100 | 100 | 90 | |
| Chickweed | 100 | 100 | 50 | 30 | |
| Corn | 70 | 50 | 40 | 0 | |
| Soybean | 100 | 100 | 90 | 80 | |
| Cotton | 100 | 100 | 100 | 100 | |
| Velvetleaf | 100 | 100 | 100 | 100 | |
| Morningglory | 100 | 100 | 80 | 80 | |
| Crabgrass | 100 | 100 | 70 | 30 | |
| Giant foxtail | 100 | 100 | 60 | 30 | |
| Barnyardgrass | 100 | 100 | 60 | 50 | |
| Johnsongrass | 100 | 90 | 30 | 20 | |
| Nutsedge | 90 | 50 | 30 | 0 | |
| Green foxtail | 100 | 90 | 60 | 30 | |
| Cocklebur | 80 | 70 | 50 | 40 | |
| Teaweed | 100 | 100 | 100 | 100 | |
| Cassia | 100 | 100 | 100 | 50 | |
| Jimsonweed | 100 | 100 | 100 | 100 | |
| Rice | 100 | 100 | 80 | 40 | |
| Cheatgrass | 90 | 60 | 50 | 40 | |

TABLE Rc

| | Compound 3 | | | | |
|---|---|---|---|---|---|
| | 62 | 16 | 4 | 1 | |
| | Preemergence | | | | g/ha |
| Spring wheat | 30 | 0 | 0 | 0 | |
| Sugarbeet | 100 | 100 | 50 | 0 | |
| Rape | 100 | 30 | 20 | 0 | |
| Wild oats | 40 | 20 | 0 | 0 | |
| Blackgrass | 70 | 60 | 0 | 0 | |
| Downy brome | 50 | 30 | 0 | 0 | |
| Lambsquarters | 100 | 100 | 90 | 80 | |
| Wild buckwheat | 100 | 100 | 60 | 30 | |
| Chickweed | 50 | 30 | 0 | 0 | |
| Corn | 100 | 80 | 0 | 0 | |
| Soybean | 80 | 70 | 40 | 20 | |
| Cotton | 100 | 20 | 0 | 0 | |
| Velvetleaf | 100 | 100 | 70 | — | |
| Morningglory | 90 | 50 | 40 | 30 | |
| Crabgrass | 100 | 100 | 70 | 60 | |
| Giant foxtail | 100 | 100 | 70 | 30 | |
| Barnyardgrass | 100 | 100 | 100 | 30 | |
| Johnsongrass | 100 | 100 | 70 | 50 | |
| Nutsedge | 100 | 100 | 100 | 100 | |
| Green foxtail | 100 | 100 | 80 | 0 | |
| Cocklebur | 60 | 50 | 30 | 30 | |
| Teaweed | 100 | 100 | 70 | 50 | |
| Cassia | 100 | 50 | 30 | — | |

TABLE Rc-continued

| | Compound 3 | | | | |
|---|---|---|---|---|---|
| | 62 | 16 | 4 | 1 | |
| | Preemergence | | | | g/ha |
| Jimsonweed | 100 | 90 | 40 | 30 | |
| Rice | 100 | 70 | 60 | 0 | |

TABLE Rd

| | Compound 3 | | | | |
|---|---|---|---|---|---|
| | 62 | 16 | 4 | 1 | |
| | Postemergence | | | | g/ha |
| Spring wheat | 80 | 20 | 0 | 0 | |
| Sugarbeet | 100 | 100 | 50 | 50 | |
| Rape | 100 | 100 | 50 | 30 | |
| Wild oats | 50 | 0 | 0 | 0 | |
| Blackgrass | 70 | 50 | 0 | 0 | |
| Downy brome | 70 | 20 | 0 | 0 | |
| Lambsquarters | 100 | 100 | 80 | 0 | |
| Wild buckwheat | 100 | 100 | 30 | 30 | |
| Chickweed | 30 | 0 | 0 | 0 | |
| Corn | 20 | 20 | 0 | 0 | |
| Soybean | 60 | 50 | 30 | 0 | |
| Cotton | 100 | 100 | 80 | 30 | |
| Velvetleaf | 100 | 70 | 60 | 30 | |
| Morningglory | 80 | 80 | 50 | 0 | |
| Crabgrass | 90 | 70 | 30 | 0 | |
| Giant foxtail | 100 | 100 | 0 | 0 | |
| Barnyardgrass | 100 | 100 | 20 | 0 | |
| Johnsongrass | 100 | 100 | 0 | 0 | |
| Nutsedge | 40 | 40 | 30 | 25 | |
| Green foxtail | 80 | 50 | 0 | 0 | |
| Cocklebur | 40 | 40 | 0 | 0 | |
| Teaweed | 100 | 50 | 50 | 40 | |
| Cassia | 70 | 50 | 30 | 0 | |
| Jimsonweed | 100 | 100 | 80 | 40 | |
| Rice | 85 | 70 | 20 | 10 | |

TABLE Re

| | Compound 4 | | | | | | |
|---|---|---|---|---|---|---|---|
| | 250 | 62 | 16 | 250 | 62 | 16 | |
| | Preemergence | | | Postemergence | | | g/ha |
| Spring wheat | 70 | 30 | 0 | — | 40 | 30 | |
| Sugarbeet | 100 | 90 | 70 | 100 | 80 | 50 | |
| Rape | 100 | 80 | 50 | 100 | 90 | 80 | |
| Wild oats | 100 | 50 | 30 | 80 | 60 | 30 | |
| Blackgrass | 100 | 70 | 30 | 100 | 80 | 40 | |
| Lambsquarters | 100 | 100 | 100 | 100 | 100 | 90 | |
| Wild buckwheat | 100 | 100 | 100 | 100 | 100 | 70 | |
| Chickweed | 60 | 30 | 0 | 50 | 0 | 0 | |
| Corn | 50 | 0 | 0 | 60 | 10 | 10 | |
| Soybean | 100 | 60 | 30 | 90 | 80 | 50 | |
| Cotton | 100 | 30 | 0 | 100 | 100 | 100 | |
| Velvetleaf | 100 | 100 | 80 | 100 | 100 | 90 | |
| Morningglory | 100 | 60 | 30 | 100 | 80 | 50 | |
| Crabgrass | 100 | 100 | 90 | 100 | 80 | 70 | |
| Giant foxtail | 100 | 100 | 70 | 90 | 80 | 60 | |
| Barnyardgrass | 100 | 100 | 90 | 100 | 100 | 60 | |
| Johnsongrass | 100 | 100 | 80 | 90 | 90 | 30 | |
| Nutsedge | 60 | 30 | 0 | 100 | 30 | 0 | |
| Green foxtail | 100 | 100 | 70 | 100 | 80 | 40 | |
| Cocklebur | 70 | 30 | 0 | 70 | 60 | 50 | |
| Teaweed | 100 | 90 | 60 | 100 | 80 | 80 | |
| Cassia | 100 | 90 | 80 | 100 | 70 | 50 | |
| Jimsonweed | 100 | 100 | 80 | 100 | 100 | 70 | |
| Rice | 70 | 40 | 0 | 100 | 90 | 30 | |
| Cheatgrass | 80 | 30 | 0 | 80 | 70 | 30 | |

TEST S

Seeds of spring wheat (*Triticum aestivum*), winter wheat (*T. aestivum*), spring barley (*Hordeum vulgare*), winter barley (*H. vulgare*), sugarbeet (*Beta vulgaris*), rape (*Brassica napus*), wild oat (*Avena fatua*), downy brome (*Bromus tectorium*), cheatgrass (*B. secalinus*), blackgrass (*Alopercurus myosuroides*), annual bluegrass (*Poa annum*), green foxtail (*Setaria viridis*), Italian ryegrass (*Lolium multiflorum*), jointed goatgrass (*Aegilops cylindrica*), *Matricaria indora*, Galium spp., Russian thistle (*Salsola kali*), lambsquarters (*Chenopodium album*), kochia (*Kochia scoparia*), black nightshade (*Solanum nigrum*), speedwell (*Veronica persica*), wild buckwheat (*Polygonium convolvulus*), viola (Viola spp.), *Veronica hederaefolia* and field pennycress (*Thlapsi arvensis*) were placed in 26 cm plastic pans containing pasteurized sandy loam soil. Plantings were maintained in the greenhouse for 28 days at which time the postemergence treatments were applied using compounds formulated in a non-phytotoxic solvent. The preemergence portion of the test was seeded just before spraying. The postemergence treatments also contained wild oats and blackgrass at 1-leaf and 3-leaf growth stages. All treatments were held in the greenhouse for an additional 21 days at which time visual assessments of plant injury were made using a scale of 0 to 100 where 0 indicates no effect, 20 indicates minimal injury and 100 indicates complete control. The variation in observed activity could be due to the fact that the tests were conducted at different times of the year or on different growth stages of plants. The results are shown in Tables Sa through Sf.

TABLE Sa

| | Compound 3 | | | | | | |
|---|---|---|---|---|---|---|---|
| | 250 | 125 | 64 | 32 | 16 | 8 | |
| | Preemergence | | | | | | g/ha |
| Spring wheat | 100 | 90 | — | 70 | 50 | 20 | |
| Winter wheat | 90 | 70 | 70 | 70 | 50 | 10 | |
| Spring barley | 80 | 80 | 70 | 50 | 30 | 20 | |
| Winter barley | 90 | 90 | 40 | 30 | 10 | 0 | |
| Sugarbeet | 100 | 100 | 100 | 100 | 100 | 100 | |
| Rape | 90 | 90 | 80 | 80 | 10 | 10 | |
| Wild oats | 100 | 90 | 70 | 60 | 30 | 10 | |
| Downy brome | 90 | 70 | 50 | 50 | 20 | 10 | |
| Cheatgrass | 90 | 70 | 70 | 30 | 10 | 0 | |
| Blackgrass | 90 | 90 | 70 | 60 | 30 | 10 | |
| Annual bluegrass | 100 | 100 | 100 | 80 | 70 | 20 | |
| Green foxtail | 100 | 100 | 100 | 100 | 100 | 80 | |
| Italian ryegrass | 100 | 100 | 90 | 90 | 70 | 60 | |
| Goatgrass | 90 | 60 | 40 | 30 | 10 | 0 | |
| *Matricaria indora* | 100 | 100 | 100 | 100 | 100 | 100 | |
| Galium | 60 | 50 | 10 | 0 | 0 | 0 | |
| Russian thistle | 100 | 100 | 100 | 100 | 90 | 70 | |
| Lambsquarters | 100 | 100 | 100 | 100 | 90 | 70 | |
| Kochia | 100 | 100 | 100 | 100 | 80 | 80 | |
| Black nightshade | 100 | 100 | 100 | 100 | 100 | 100 | |
| Speedwell | 100 | 100 | 100 | 100 | 90 | 70 | |
| *Veronica hederaefolia* | 100 | 100 | 100 | 100 | 60 | 30 | |
| Wild buckwheat | 100 | 100 | 100 | 100 | 100 | 100 | |
| Viola | 100 | 100 | 100 | 100 | 100 | 60 | |
| Field pennycress | 100 | 100 | 100 | 100 | 100 | 100 | |

TABLE Sb

| | Compound 3 | | | | | | |
|---|---|---|---|---|---|---|---|
| | 250 | 125 | 64 | 32 | 16 | 8 | |
| | Postemergence | | | | | | g/ha |
| Spring wheat | 100 | 50 | 40 | 10 | 10 | 10 | |
| Winter wheat | 70 | 70 | 20 | 10 | 10 | 10 | |
| Spring barley | 60 | 30 | 10 | 10 | 10 | 10 | |
| Winter barley | 100 | 70 | 20 | 20 | 10 | 10 | |
| Sugarbeet | 100 | 100 | 80 | 70 | 50 | 30 | |
| Rape | 100 | 80 | 70 | 70 | 70 | 60 | |
| Wild oats 1-leaf | 100 | 70 | 70 | 50 | 20 | 10 | |
| 3-leaf | 70 | 30 | 10 | 10 | 10 | 10 | |
| Downy brome | 30 | 10 | 10 | 0 | 0 | 0 | |
| Cheatgrass | 50 | 30 | 10 | 0 | 0 | 0 | |
| Blackgrass 1-leaf | 80 | 20 | 20 | 10 | 0 | 0 | |
| 3-leaf | 90 | 30 | 10 | 10 | 10 | 0 | |
| Annual bluegrass | 40 | 20 | 10 | 0 | 0 | 0 | |

TABLE Sb-continued

| | Compound 3 | | | | | | |
|---|---|---|---|---|---|---|---|
| | 250 | 125 | 64 | 32 | 16 | 8 | |
| | Postemergence | | | | | | g/ha |
| Green foxtail | 100 | 100 | 80 | 20 | 0 | 0 | |
| Italian ryegrass | 100 | 80 | 60 | 10 | 10 | 0 | |
| Goatgrass | 30 | 10 | 10 | 10 | 10 | 0 | |
| *Matricaria indora* | 100 | 100 | 100 | 100 | 100 | 100 | |
| Galium | 100 | 70 | 60 | 30 | 30 | 10 | |
| Russian thistle | 100 | 100 | 100 | 100 | 80 | 60 | |
| Lambsquarters | 100 | 100 | 100 | 90 | 90 | 20 | |
| Kochia | 100 | 100 | 100 | 100 | 100 | 80 | |
| Black nightshade | 100 | 100 | 100 | 100 | 100 | 100 | |
| Speedwell | 100 | 100 | 100 | 40 | 40 | 10 | |
| *Veronica hederaefolia* | 100 | 100 | 100 | 60 | 20 | 0 | |
| Wild buckwheat | 100 | 100 | 100 | 100 | 80 | 10 | |
| Viola | 100 | 100 | 100 | 100 | 100 | 100 | |
| Field pennycress | 100 | 100 | 100 | 100 | 100 | 100 | |

TABLE Sc

| | Compound 3 | | | | | | |
|---|---|---|---|---|---|---|---|
| | 250 | 125 | 64 | 32 | 16 | 8 | |
| | Preemergence | | | | | | g/ha |
| Spring wheat | 100 | 95 | 95 | 70 | 65 | 35 | |
| Winter wheat | 100 | 100 | 95 | 70 | 65 | 50 | |
| Spring barley | 100 | 90 | 80 | 70 | 65 | 45 | |
| Winter barley | 100 | 95 | 95 | 80 | 65 | 40 | |
| Sugarbeet | 100 | 100 | 100 | 95 | 95 | 90 | |
| Rape | 100 | 100 | 100 | 90 | 80 | 65 | |
| Wild oats | 100 | 100 | 100 | 60 | 60 | 35 | |
| Downy brome | 70 | 75 | 50 | 25 | 10 | 5 | |
| Cheatgrass | 90 | 95 | 80 | 55 | 55 | 30 | |
| Blackgrass | 100 | 100 | 90 | 60 | 55 | 30 | |
| Annual bluegrass | 100 | 100 | 95 | 80 | 75 | 55 | |
| Green foxtail | 100 | 100 | 100 | 100 | 100 | 95 | |
| Italian ryegrass | 100 | 100 | 100 | 80 | 75 | 65 | |
| Goatgrass | 90 | 75 | 55 | 20 | 0 | 0 | |
| *Matricaria indora* | 100 | 100 | 100 | 100 | 100 | 90 | |
| Galium | 70 | 30 | 10 | 10 | 5 | 5 | |
| Russian thistle | 100 | 100 | 65 | 65 | 40 | 35 | |
| Lambsquarters | 100 | 100 | 100 | 100 | 100 | 85 | |
| Kochia | 100 | 100 | 100 | 100 | 95 | 85 | |
| Black nightshade | 100 | 100 | 100 | 100 | 100 | 100 | |
| Speedwell | 100 | 100 | 100 | 95 | 80 | 65 | |
| *Veronica hederaefolia* | 100 | 100 | 100 | 95 | 80 | 65 | |
| Wild buckwheat | 100 | 100 | 100 | 100 | 100 | 80 | |
| Viola | 100 | 100 | 100 | 100 | 95 | 90 | |
| Field pennycress | 100 | 100 | 100 | 100 | 100 | 95 | |

TABLE Sd

| | Compound 3 | | | | | | |
|---|---|---|---|---|---|---|---|
| | 250 | 125 | 64 | 32 | 16 | 8 | |
| | Postemergence | | | | | | g/ha |
| Spring wheat | 40 | 35 | 25 | 15 | 15 | 15 | |
| Winter wheat | 70 | 60 | 50 | 30 | 15 | 15 | |
| Spring barley | 80 | 90 | 75 | 40 | 30 | 20 | |
| Winter barley | 60 | 55 | 40 | 20 | 10 | 10 | |
| Sugarbeet | 100 | 100 | 100 | 100 | 85 | 75 | |
| Rape | 100 | 100 | 95 | 80 | 75 | 55 | |
| Wild oats 1-leaf | 100 | 90 | 85 | 50 | 25 | 10 | |
| 3-leaf | 100 | 90 | 55 | 30 | 15 | 10 | |
| Downy brome | 40 | 30 | 20 | 20 | 10 | 10 | |
| Cheatgrass | 60 | 75 | 45 | 30 | 10 | 10 | |
| Blackgrass 1-leaf | 100 | 100 | 45 | 20 | 15 | 10 | |
| 3-leaf | 60 | 20 | 10 | 10 | 10 | 10 | |
| Annual bluegrass | 80 | 85 | 60 | 20 | 10 | 10 | |
| Green foxtail | 100 | 100 | 100 | 100 | 100 | 100 | |
| Italian ryegrass | 90 | 95 | 80 | 55 | 15 | 10 | |
| Goatgrass | 50 | 75 | 45 | 25 | 15 | 10 | |
| *Matricaria indora* | 100 | 100 | 100 | 100 | 65 | 40 | |
| Galium | 70 | 75 | 50 | 40 | 30 | 10 | |
| Russian thistle | 100 | 100 | 100 | 95 | 85 | 70 | |
| Lambsquarters | 100 | 100 | 95 | 90 | 80 | 60 | |
| Kochia | 100 | 100 | 100 | 100 | 90 | 75 | |
| Black nightshade | 100 | 100 | 100 | 85 | 85 | 75 | |

TABLE Sd-continued

| | Compound 3 | | | | | | |
|---|---|---|---|---|---|---|---|
| | 250 | 125 | 64 | 32 | 16 | 8 | |
| | Postemergence | | | | | | g/ha |
| Speedwell | 100 | 100 | 100 | 60 | 50 | 20 | |
| Veronica hederaefolia | 100 | 85 | 65 | 30 | 10 | 0 | |
| Wild buckwheat | 100 | 100 | 100 | 100 | 85 | 50 | |
| Viola | 100 | 95 | 85 | 75 | 40 | 15 | |
| Field pennycress | 100 | 100 | 85 | 85 | 65 | 30 | |

TABLE Se

| | Compound 3 | | | | | |
|---|---|---|---|---|---|---|
| | 250 | 125 | 64 | 32 | 16 | |
| | Preemergence | | | | | g/ha |
| Spring wheat | 90 | 90 | 80 | 70 | 50 | |
| Winter wheat | 90 | 90 | 90 | 80 | 60 | |
| Spring barley | 80 | 80 | 80 | 80 | 70 | |
| Winter barley | 80 | 60 | 60 | 40 | 20 | |
| Sugarbeet | 100 | 100 | 100 | 100 | 100 | |
| Rape | 100 | 100 | 100 | 100 | 90 | |
| Wild oats | 100 | 100 | 100 | 90 | 70 | |
| Downy brome | 60 | 30 | 30 | 20 | 0 | |
| Cheatgrass | 80 | 20 | 20 | 20 | 10 | |
| Blackgrass | 100 | 90 | 90 | 90 | 80 | |
| Annual bluegrass | 100 | 100 | 100 | 90 | 80 | |
| Green foxtail | 100 | 100 | 100 | 100 | 100 | |
| Italian ryegrass | 100 | 100 | 100 | 90 | 50 | |
| Goatgrass | 30 | 30 | 20 | 20 | 0 | |
| Matricaria indora | 100 | 100 | 100 | 100 | 100 | |
| Galium | 80 | 70 | 70 | 50 | 40 | |
| Russian thistle | 100 | 100 | 100 | 100 | 80 | |
| Lambsquarters | 100 | 100 | 100 | 100 | 100 | |
| Kochia | 100 | 100 | 100 | 100 | 100 | |
| Black nightshade | 100 | 100 | 100 | 100 | 100 | |
| Speedwell | 100 | 100 | 100 | 100 | 80 | |
| Veronica hederaefolia | 100 | 100 | 80 | 80 | 60 | |
| Wild buckwheat | 100 | 100 | 100 | 100 | 100 | |
| Viola | 100 | 100 | 100 | 90 | 90 | |
| Field pennycress | 100 | 100 | 100 | 100 | 100 | |

TABLE Sf

| | Compound 3 | | | | | |
|---|---|---|---|---|---|---|
| | 250 | 125 | 64 | 32 | 16 | |
| | Postemergence | | | | | g/ha |
| Spring wheat | 30 | 30 | 30 | 30 | 20 | |
| Winter wheat | 70 | 50 | 40 | 40 | 20 | |
| Spring barley | 80 | 60 | 60 | 50 | 30 | |
| Winter barley | 80 | 50 | 40 | 40 | 20 | |
| Sugarbeet | 100 | 100 | 100 | 90 | 60 | |
| Rape | 100 | 100 | 90 | 90 | 40 | |
| Wild oats 1-leaf | 100 | 100 | 50 | 50 | 30 | |
| 3-leaf | 100 | 100 | 40 | 20 | 0 | |
| Downy brome | 30 | 30 | 30 | 20 | 20 | |
| Cheatgrass | 100 | 90 | 70 | 50 | 20 | |
| Blackgrass 1-leaf | 100 | 80 | 50 | 50 | 20 | |
| 3-leaf | 80 | 60 | 30 | 30 | 10 | |
| Annual bluegrass | 100 | 90 | 70 | 30 | 20 | |
| Green foxtail | 100 | 100 | 100 | 100 | 70 | |
| Italian ryegrass | 100 | 100 | 100 | 80 | 20 | |
| Goatgrass | 90 | 90 | 50 | 50 | 20 | |
| Matricaria indora | 100 | 100 | 100 | 60 | 10 | |
| Galium | 100 | 70 | 50 | 50 | 20 | |
| Russian thistle | 100 | 100 | 100 | 100 | 40 | |
| Lambsquarters | 100 | 100 | 100 | 70 | 20 | |
| Kochia | 100 | 100 | 100 | 80 | 60 | |
| Black nightshade | 100 | 100 | 100 | 100 | 70 | |
| Speedwell | 100 | 100 | 100 | 90 | 20 | |
| Veronica hederaefolia | 100 | 100 | 60 | 60 | 10 | |
| Wild buckwheat | 100 | 100 | 100 | 100 | 30 | |
| Viola | 100 | 100 | 100 | 100 | 0 | |
| Field pennycress | 100 | 100 | 100 | 100 | 10 | |

TEST U

Plastic pots were partially filled with silt loam soil. The soil was then saturated with water. Japonica rice (*Oryza sativa*) seedlings at the 2.0 to 2.5 leaf stage; seeds of barnyardgrass (*Echinochloa crus-galli*), duck salad (*Heteranthera limosa*), and umbrella sedge (*Cyperus difformis*); and tubers of arrowhead (Sagittaria spp.), and waterchestnut (Eleocharis spp.) were planted into this soil. Several days after planting, water levels were raised to 3 cm above the soil surface and maintained at this level throughout the test. Chemical treatments were formulated in a non-phytotoxic solvent and applied directly to the paddy water. Treated plants and untreated controls were maintained in a greenhouse for approximately 21 days, after which all treated plants were compared to untreated control and visually evaluated for injury. Plant response ratings, summarized in Table Ua, are reported on a zero to 10 scale where zero is no effect and 10 is complete control.

TABLE Ua

| | Compound 1 | | | | | |
|---|---|---|---|---|---|---|
| | 500 | 250 | 125 | 64 | 32 | g/ha |
| Japonica rice | 100 | 98 | 90 | 70 | 70 | |
| Barnyardgrass | 100 | 100 | 100 | 80 | 90 | |
| Water chestnut | 100 | 80 | 60 | 50 | 50 | |
| Arrowhead | 100 | 100 | 100 | 60 | 20 | |
| Duck salad | 100 | 100 | 100 | 100 | 100 | |
| Umbrella sedge | 100 | 100 | 100 | 100 | 100 | |

TEST V

The Corn and Sorghum Herbicide Test included the following species in both the preemergence and postemergence evaluations:

| | SPECIES | |
|---|---|---|
| Category | Common Name | Scientific Name |
| Crops | Corn | Zea mays |
| | Soybean | Glycine max |
| | Sorghum | Sorghum bicolor |
| Grasses | Green foxtail | Setaria viridis |
| | Giant foxtail | Setaria faberii |
| | Johnsongrass | Sorghum halepense |
| | Barnyardgrass | Echinochloa crus-galli |
| | Fall panicum | Panicum dichotomiflorum |
| | Crabgrass | Digitaria sanguinalis |
| | Nutsedge | Cyperus rotundus |
| Broadleaves | Cocklebur | Xanthium pensylvanicum |
| | Morningglory | Ipomoea hederacea |
| | Velvetleaf | Abutilon theophrasti |
| | Jimsonweed | Datura stramonium |
| | Lambsquarters | Chenopodium album |
| | Pigweed | Amaranthus retroflexus |
| | Smartweed | Polygonum persicaris |

Postemergence

Postemergence plantings were grown in Sassafras sandy loam soil. Corn and soybeans were grown in separate 25 cm diameter containers. Sorghum and the seven grass weed species were grown in two 18 cm diameter containers, 4 species per container. The seven broadleaf weed species were also grown in two 18 cm diameter containers, 4 species in one container, 3 species in the second container. One additional planting of corn in an 18 cm diameter container was made. The soil surface of this additional container of corn was covered with the absorbent, perlite, before spray treatment so that test chemicals would enter the plant only via the foliage. The plants were grown 10–21 days, dependent upon the species and then sprayed postemergence with the test chemicals dissolved in a non-phytotoxic solvent.

Preemergence

Preemergence plantings were grown in fertilized Tama silt loam soil. These plantings are identical to those described in the postemergence section, with the exception of the corn planting having perlite covering the soil surface. These plantings were made the day of or the day before spraying the test chemicals dissolved in a non-phytotoxic solvent.

Treated plants and controls were maintained in the greenhouse for 2 to 4 weeks. Visual ratings were made using a scale of 0 to 100 where 0 indicates no effect, and 100 indicates complete control. The results are shown in Tables Va and Vb.

TABLE Va

| | Compound 1 | | | | | |
|---|---|---|---|---|---|---|
| | 64 | 32 | 16 | 8 | 4 | 2 |
| | | | Postemergence | | | g/ha |
| Corn | 50 | 30 | 10 | 0 | 0 | 0 |
| Sorghum | 100 | 100 | 20 | 0 | 0 | 0 |
| Soybean | 70 | 60 | 20 | 10 | 10 | 0 |
| Green foxtail | 60 | 40 | 30 | 0 | 0 | 0 |
| Giant foxtail | 90 | 60 | 30 | 0 | 0 | 0 |
| Fall panicum | 95 | 50 | 30 | 0 | 0 | 0 |
| Crabgrass | 50 | 20 | 0 | 0 | 0 | 0 |
| Barnyardgrass | 100 | 100 | 20 | 0 | 0 | 0 |
| Johnsongrass | 100 | 90 | 20 | 20 | 0 | 0 |
| Velvetleaf | 100 | 100 | 100 | 20 | 0 | 0 |
| Cocklebur | 50 | 50 | 50 | 20 | 0 | 0 |
| Smartweed | 100 | 100 | 40 | 0 | 0 | 0 |
| Lambsquarters | 100 | 95 | 50 | 50 | 30 | 20 |
| Pigweed | 100 | 60 | 0 | 0 | 0 | 0 |
| Ivyleaf morning-glory | 90 | 20 | 50 | 30 | 0 | 0 |
| Jimsonweed | 100 | 100 | 70 | 100 | 50 | 50 |
| Corn* | 30 | 10 | 0 | 0 | 0 | 0 |

*soil covered with perilite at time of postemergence treatment

TABLE Vb

| | Compound 1 | | | |
|---|---|---|---|---|
| | 250 | 125 | 64 | |
| | | Preemergence | | g/ha |
| Corn | 70 | 65 | 50 | |
| Sorghum | 100 | 70 | 50 | |
| Soybean | 100 | 100 | 55 | |
| Green foxtail | 100 | 100 | 100 | |
| Giant foxtail | 100 | 100 | 100 | |
| Fall panicum | 100 | 100 | 100 | |
| Crabgrass | 100 | 100 | 100 | |
| Barnyardgrass | 100 | 100 | 100 | |
| Johnsongrass | 100 | 100 | 100 | |
| Nutsedge | 65 | 55 | 25 | |
| Velvetleaf | 100 | 100 | 85 | |
| Cocklebur | 55 | 25 | 0 | |
| Smartweed | 100 | 100 | 100 | |
| Lambsquarters | 100 | 100 | 100 | |
| Pigweed | 100 | 100 | 100 | |
| Ivyleaf morninggglory | 45 | 35 | 20 | |
| Jimsonweed | 100 | 100 | 100 | |

TEST W

Sugarcane plants growing in 20.3 cm plastic pots were cut back to stimulate ratoon growth. At the early ratoon stage the pots were seeded with itchgrass (*R. cochinchinensis*), guineagrass (*P. maximum*) and large crabgrass (*D. sanguinalis*) seeds.

The pots were sprayed with Compound 1 formulated in a non-phytotoxic spray solvent. The treatments were postemergence to the sugarcane and preemergence to the weed seeds. Plants were visually rated 65 DAT and compared with the appropriate controls. The injury rating scale used in Test G was also used here. The results are shown in Table W.

TABLE W

| | Compound 1 | |
|---|---|---|
| | 250 | g/ha |
| Postemergence Sugarcane | 0 | |
| Preemergence | | |
| Itchgrass | 100 | |
| Guineagrass | 100 | |
| Large crabgrass | 100 | |

TEST X

Banana (Musa sp.) plants growing in 20.3 cm pots were used in this test. Plants at the 11-leaf stage were sprayed with Compound 1 in a non-phytotoxic solvent. The treatments were applied over-the-top in one group of plants and post-directed to simulate field type treatment in another group. Treated plants were visually rated 54 DAT and compared with the appropriate controls. The injury rating scale used in Test W was also used here. The results are shown in Table X.

TABLE X

| | Compound 1 | | | |
|---|---|---|---|---|
| | 250 | 125 | 64 | g/ha |
| Over-the-top Banana | 20* | 0 | 0 | |
| Post-directed Banana | 0 | 0 | 0 | |

*main stem died but healthy side suckers developed.

What is claimed is:

1. A method for controlling weeds in plantation crops which comprises applying to the locus of the weeds a herbicidally effective amount of

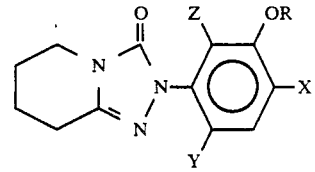

I wherein
R is isopropyl, allyl, propargyl or —CH(CH₃)C≡CH;
X is Cl or Br;
Y is F or Cl;
Z is H or can be taken together with R as

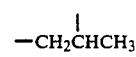

such that the linking oxygen is attached to the methine carbon.

2. A method of claim 1 which comprises applying to the locus of the weeds a herbicidally effective amount of a compound of Formula I wherein X is Cl, Y is Cl and Z is H.

3. A method of claim 2 wherein the plantation crop is selected from citrus, sugarcane, coffee, banana, oil palm, rubber and loblolly pine.

4. A method of claim 2 wherein the compound is 2-[2,4-dichloro-5-[(2-propynyl)oxy]phenyl]-5,6,7,8-tetrahydro-1,2,4-triazolo-[4,3-a]-pyridin-3(H)-one.

5. A method of claim 4 wherein the plantation crop is citrus.

6. A method of claim 4 wherein the plantation crop is sugarcane.

7. A method of claim 4 wherein the plantation crop is coffee.

8. A method of claim 4 wherein the plantation crop is banana.

9. A method of claim 4 wherein the plantation crop is oil palm.

10. A method of claim 4 wherein the plantation crop is rubber.

11. A method of claim 4 wherein the plantation crop is loblolly pine and the compound is applied preemergent.

12. A method of claim 4 wherein the plantation crop is grapes.

* * * * *

UNITED STATES PATENT AND TRADEMARK OFFICE
CERTIFICATE OF CORRECTION

PATENT NO. : 5,332,718
DATED : JULY 26, 1994
INVENTOR(S) : KOFI S. AMUTI

It is certified that error appears in the above-identified patent and that said Letters Patent is hereby corrected as shown below:

Column 1, line 54
  Change "methane" to --methine--

Column 7, line 31
  Change "control of oil vegetation" to --control of all vegetation--

Column 12, line 29
  Change "*Pueraria iavancia*" to -- *Pueraria javanica* --

Column 13, line 28
  Change "pecan (Carva spp.)," to --pecan (Carya spp.), --

UNITED STATES PATENT AND TRADEMARK OFFICE
CERTIFICATE OF CORRECTION

PATENT NO. : 5,332,718

DATED : JULY 26, 1994

INVENTOR(S) : KOFI S. AMUTI

It is certified that error appears in the above-identified patent and that said Letters Patent is hereby corrected as shown below:

Column 15, Table H, lines 21-22

Change
"Postemergence    0    0    0    0
  Citrus "

to
-- Postemergence
  Citrus            0    0    0    0 --

Column 36, Table W, lines 5-6

Change
"Postemergence    0
  Sugarcane"

to
-- Postemergence
  Sugarcane      0 --

UNITED STATES PATENT AND TRADEMARK OFFICE
CERTIFICATE OF CORRECTION

PATENT NO. : 5,332,718

DATED : JULY 26, 1994

INVENTOR(S) : KOFI S. AMUTI

It is certified that error appears in the above-identified patent and that said Letters Patent is hereby corrected as shown below:

<u>Column 36, Table X, lines 26-29</u>

Change

"Over-the-top

| | | | |
|---|---|---|---|
| Banana | 20 * | 0 | 0 |
| Post-directed | | | |
| Banana " | 0 | 0 | 0 | to

-- <u>Over-the-top</u>

| | | | |
|---|---|---|---|
| Banana | 20* | 0 | 0 |
| <u>Post-directed</u> | | | |
| Banana | 0 | 0 | 0 -- |

Signed and Sealed this

Twenty-ninth Day of August, 1995

Attest:

BRUCE LEHMAN

*Attesting Officer*  *Commissioner of Patents and Trademarks*